United States Patent [19]
Cook et al.

[11] Patent Number: 5,623,070
[45] Date of Patent: Apr. 22, 1997

[54] HETEROATOMIC OLIGONUCLEOSIDE LINKAGES

[75] Inventors: Phillip D. Cook; Yogesh S. Sanghvi, both of Carlsbad, Calif.

[73] Assignee: Isis Pharmaceuticals, Inc., Carlsbad, Calif.

[21] Appl. No.: 395,168

[22] Filed: Feb. 27, 1995

Related U.S. Application Data

[63] Continuation of Ser. No. 903,160, filed as PCT/US92/04294, May 21, 1992, abandoned, which is a continuation-in-part of Ser. No. 703,619, May 21, 1991, Pat. No. 5,378,825, which is a continuation-in-part of Ser. No. 566,836, Aug. 13, 1990, Pat. No. 5,223,618, and Ser. No. 558,663, Jul. 27, 1990, Pat. No. 5,138,045.

[51] Int. Cl.$^6$ .................... C07H 19/06; C07H 19/167; C07H 19/173; C07H 21/00
[52] U.S. Cl. .................. 536/27.6; 536/23.1; 536/25.3; 536/27.89; 536/28.5; 536/28.54
[58] Field of Search ................ 536/23.1, 24.1, 536/25.3, 24.5, 27.14, 27.21, 27.23, 27.3, 27.6, 27.8, 27.81, 28.4, 28.2, 28.5, 28.53, 28.54

[56] References Cited

FOREIGN PATENT DOCUMENTS

| | | |
|---|---|---|
| 0287313 | 10/1988 | European Pat. Off. . |
| 0378518 | 7/1990 | European Pat. Off. . |
| 0381335 | 8/1990 | European Pat. Off. . |
| 0417999 | 3/1991 | European Pat. Off. . |
| WO89/11486 | 11/1989 | WIPO . |
| WO89/12060 | 12/1989 | WIPO . |
| WO90/08156 | 7/1990 | WIPO . |
| WO92/02534 | 2/1992 | WIPO . |
| WO92/05186 | 4/1992 | WIPO . |
| WO92/20822 | 11/1992 | WIPO . |

OTHER PUBLICATIONS

Gura "Antisense has Growing Pains" Science 270 (1995) pp. 575–577.
Beaucage et al. (1993) Tetrahedron vol. 49: 6123–6177.
Sanghvi et al. (1993) Nucleosides and Nucleotides as Antitumor and Antiviral Agents. ed. C.K. Chu & D.C. Baker, Plenum Press, New York.
Stein et al. (1993) Science vol. 261: 1004–1012.
Koole et al. (1987) Proceedings of the Koninklijke Nederlandse Akademic van Wetenschappen vol. 90(1): 41–46.
Kondo et al. (1985) Nuc. Acid. Res. Symposium Series No. 16: 93–96.
Montgomery et al. (1981) Nuc. Acid. Res. Symposium Series No. 9: 95–97.
Secrist et al. (1990) Nucleosides Nucleotides vol. 9(4): 619–627.
Montgomery et al. (1984) J. Med. Chem. vol. 27(5): 680–684.
Barton et al., A "One–Pot" Synthesis of Sulfenamides, J. Org. Chem., 1991, 56:6702.
Camarasa et al. Aldol Reaction of Nucleoside 5'–Carboxaldehydes with Acetone–Synthesis of 5'–C–Chain Extended Thymidine Derivatives, Nucleosides and Nucleotides, 1990, 9:533.
Cosstick et al., Synthesis and properties of Dithymidine Phosphate Analogues Containing 3'–Thiothymidine, Nucleic Acids Res., 1990, 18:829.
Etzold et al., The Extension of the Sugar Chain of Thymidine: a New Route to 5'–Deoxyhexose nucleosides, Chemical Communications, 1968, 422.
Fleet et al., Methyl 5-0-Tert-Butyldiphenylsilyl-2-Deoxy-αβ-D-threo-Pentofuranoside as a Divergent Intermediate for the Synthesis of 3'–Substituted-2', 3'–Dideoxynucleosides: Synthesis of 3'–Azido-3'–Deoxythymidine, 3'–Deoxy-3'–Flurothymidine and 3'–Cyano-3'–Deoxythymidine, Tetrahedron, 1988, 44:625.
Gait M.J., ed., Oligonucleotide Synthesis, A Practical Approach (IRL Press 1984).
Horwitz et al., Nucleosides. V. The Monomesylates of 1-(2'–Deoxy-β-D-Lyxofuranosyl) Thymine, J. Org. Chem., 1964, 29:2076.
Jones et al., Synthesis of Carbocyclic Nucleosides: Preparation of (–)-5'–Homoaristeromycin and Analogues, J. Chem. Soc. Perkin Trans., 1988, 1:2927.
Bankston et al., A Short Synthesis of 5'–O–Trityl–Protected thero–and erythro-3'–Cyano-3'–deoxythymidine Epimers, J. Het. Chem., (1992) vol. 29, pp. 1405–1407.
Beaucage et al., Advances in the Synthesis of Oligonucleotides by the Phosphoramidite Approach, Tetrahedron, (1992), vol. 48, No. 12, pp. 2223–2311.
Comprehensive Organic Synthesis: Ed. by B.M. Trost & J. Fleming, vol. 4, p. 760.
Debart et al., Intermolecular Radical C–C Bond Formation: Synthesis of a Novel Dinucleoside Linker for Non–anionic Antisense Oligonucleosides, Tetrahedron Ltrs., (1992) vol. 33, No. 19, pp. 2645–2648.
Fiandor et al., Tetrahedron Letts., 1990, 33:597.
Hata et al., J. Chem. Soc. Perkin I, 1980, 306.
Hillgartner et al., Bis(trimethylzinn)benzpinakolat, seine reversible radialische Dissoziation und Reaktionen, Liebigs Ann. Chem., (1975), 586–599.
Hronowski et al., Synthesis of New Carbocyclic Analogues of 3' –Azido-and 3'–Amino-2', 3'–dideoxynucleosides, J. Chem. Sox., Chem. Commun., (1990) pp. 1547–1548.

(List continued on next page.)

*Primary Examiner*—George C. Elliott
*Assistant Examiner*—Thomas G. Larson
*Attorney, Agent, or Firm*—Woodcock Washburn Kurtz Mackiewicz & Norris

[57] ABSTRACT

Oligonucleotide-mimicking macromolecules that have improved nuclease resistance are provided. Replacement of the normal phosphorodiester inter-sugar linkages found in natural oligonucleotides with three or four atom linking groups provide unique oligonucleotide-mimicking macromolecules that are useful in regulating RNA expression and in therapeutics. Methods of synthesis and use also are disclosed.

8 Claims, No Drawings

OTHER PUBLICATIONS

Vasseur et al., Oligonucleosides: Synthesis of a Novel, J. Am. Chem. Soc., (1992), vol. 114, pp. 4006, 4007.

Koster et al., Dialkyl Aluminum Chloride, Tetrahedron Ltrs., (1982), vol. 23, No. 26, pp. 2641–2644.

Lim et al., Book of Abstracts, 203 ACS national Meeting, San Francisco, CA., Apr. 5–10, 1992, of the procedure of Hill, et al., J. Chem. Soc., 1964, 3709.

Moffatt et al., The Synthesis of 6' –Deoxyhomonucleoside–6' –phosphonic Acids, J. Am. Chem. Soc., (1968), vol. 90, pp. 5337–5338.

Nicolaoi et al., Carbocylic Thromboxane $A_2{}^1$, J. Am. Chem. Soc., 102:4 (1980) pp. 1404–1409.

Shaw et al., Modified deoxyoligonucleotides stable to exonuclease degradation in serum, Nucleic Acids Res., vol. 19, No. 4, (1991) pp. 747–750.

Nucleosides and Nucleotides, 1990, 9:533.

Nucleosides & Nucleotides, 1990, 9:89.

Poopeiko, et al., Syn. Lett., 1991, 342.

Secrist et al., Abstract 21, Synthesis and Biological Activity of 4'-Thionucleosides, Program & Abstracts, Tenth International Roundtable, Nucleosides, Nucleotides and their Biological Applications, Park City, Utah, Sep. 16–20, 1992.

Wu et al., New Synthesis of 2'-3'-Dideoxy-3'C-Cyano-2'-Substituted Thymidines by Michael Additiona Reac-tions, Tet. Lts., (1989), vol. 45, No. 3, pp. 855–862.

Parkes et al., A Short Synthesis of 3'-Cyano-3'-Deoxythymidine, Tetrahedron Lts., (1988) vol. 29, No. 24, pp. 2995–2996.

Verheyden et al., Halo Sugar Nucleosides. II., J. Org. Chem., (1970), vol. 35, No. 9 pp. 2868–2877.

Yang et al., Construction of Glycosidic N–O Linkages in oligosaccharides, J. Am. Chem. Soc., (1991), vol. 113, pp. 4715–4716.

Heinemann, U. et al., "Effect of a Single 3'-methylene Phosphonate Linkage on the Conformation of an A–DNA Octamer Double Helix", *Nucleic Acids Res.* 1991, 19(3), 427–433.

Morr, M. et al., "Building Blocks for the Chemical Synthesis of DNA Containing $C(3')$–$CH_2$–P Bonds", in Chemical Synthesis in Molecular Biology, GBF (Gesellschaft fuer Biotechnologische Forschung Braunschweig–Stoeckheim), Bloecker et al, eds., 1987, vol. 8, pp. 107–113.

Barton, D. et al., "Stereoselectivity in radical reactions of 2'-deoxynucleosides. A synthesis of an isostere of 3'-azido-3'-deoxythymidine-5'-monophosphate (AZT-5' monophosphate)", *Tetrahedron Letters* 1989, 30(37), 4969–4972.

Cormier et al., "Synthesis of hexanucleotide analogues containing diisopropylsilyl internucleotide linkages", *Nucleic Acids Research* 1988, 16, 4583–4594.

Curran, D.P., "Radical Addition Reactions", in Comprehensive Organic Synthesis, Trost, B.M. and Fleming, I. Eds., vol. 4. pp. 715–823 Pergamon Press, Oxford (1991).

Fikes, L. et al., "Presassociating α–Nucleophiles", *J. Am. Chem. Soc.* 1992, 114, 1493–1495.

Goodchild, J. et al., "Conjugates of Oligonucleotides and Modified Oligonucleotides: A Review of Their Synthesis and Properties", *Bioconjugate Chemistry* 1990, 1(3), 165–187.

Halford and Jones, "Synthesis Analogues of Polynucleotides", *Nature* 1968, 217, 638–640.

Jenkins, S.R. and Walton, E., "[52] 9–(2–methyl–β–D–ribofuranosyl)adenine (2'–methyladenosine)" in *Synthetic Procedures in Nucleic Acid Chemistry,* Zorbach and Tipson, eds., vol. 1, pp. 149–153, Wiley & Sons.

Kirschenbaum, M.R. et al., "Novel oligonucleotide analogues with a sulfur–based linkage", *The Fifth San Diego Conference on Nucleic Acids: New Frontiers, American Association for Clinical Chemistry* Nov. 14–15, 1990, Poster 28.

Motawia, M. and Pederson, "A New Route to 2',3'–Dideoxycytidine", *Liebigs Ann. Chem.* 1990, 599–602.

Sproat, B.S. et al., "2'–O–Methyloligoribonucleotides: Synthesis and Applications", in Oligonucleotides and Analogues—A Practical Approach, Eckstein, F., ed., Oxford University Press, Oxford, 1991, pp. 49–86.

Zon and Stec, "Phosphorothioate Oligonucleotides", Oligonucleotides and Analogs: A Practical Approach, F. Eckstein, Ed., IRL Press, Chapter 4 87–108 (1991).

Debart, F. et al., "Intermolecular Radical C–C Bond Formation: Synthesis of a Novel Dinucleoside Linker for Non–Anionic Antisense Oligonucleosides", *Tetrahedron Letters* 1992, 33(19), 2645–2648.

Etzold, G. et al., "The Extension of the Sugar Chain of Thymidine: A New Route to 5'–Deoxyhexose Nucleosides", *Chemical Communications* 1968, p. 422.

Goodchild, J., "Inhibition of Gene Expression by Oligonucleotides", in Oligonucleotides, CRC Press, USA, 1989, pp. 53–78.

Kondo, K. et al., "Synthesis of 5'(e')–O–amino Nucleosides", *Nucleic Acids Research Symposium Series No. 16,* 1985, 93–96.

Koole, L. et al., "Enhanced Stability of a Watson & Crick DNA Duplex Structure by Methylation of the Phosphate Groups in One Strand", *Proceedings of the Koninklijke Nederlandse Akademie van Wetenschappen* 1987, 90(1), 41–46.

Montgomery, J. and Thomas, "Nucleosides Containing Chemically Reactive Groups. 2. Chloromethylketo Derivatives of Pyrimidine Nucleosides", *Nucleic Acids Research Symposium Series No. 9,* 1981, 95–97.

Montgomery, J. et al., "Potential Inhibitors of Nucleotide Biosynthesis. 2. Halomethyl Ketone Derivatives of Pyrimidine Nucleosides", *J. Med. Chem.* 1984, 27, 680–684.

Rawson, T. and Webb, "The Synthesis of 5'–Homo–2'–Deoxycytidine", *Nucleosides & Nucleotides* 1990, 9(1), 89–96.

Secrist III, J. et al., "5'–C'–Chain-Extended Adenosine Derivatives Related to Sinefungin. SYnthesis and Biological Activity", *Nucleosides & Nucleotides* 1990, 9(4), 619–627.

Vasseur, J. et al., "Oligonucleosides: Synthesis of a Novel Methylhydroxylamine–Linked Nucleoside Dimer and Its Incorporation Into Antisense Sequences", *J. Am. Chem. Soc.* 1992, 114, 4007–4008.

Miller, et al., *Biochemistry,* 1981, 20, 1874–1880.

Coull, et al., *Tetrahedron Letters,* vol. 28, No. 7, 1987, 745–748.

van der Krol, et al., *BioTechniques,* vol. 6, No. 10, 1988, 958–976.

Matteucci, *Tetrahedron Letters,* vol. 31., No. 17, 1991, 2385–2388.

Quaedflieg, G.A., et al., *Recl. Trav. Chim Pays–Bas,* 1991, 110, 435–436.

Miller, P.S., *Biotechnology,* vol. 9, 1991 358–362.

Nicolaou, et al., *J. Am. Chem. Soc.,* 1983, 105, 2430–2434.
Huang, Z., et al., *J. Org. Chem.,* 1991, 56, 3869–3882.
Stirchak, E.P. and Summerton, J.E., *J. Org. Chem.,* 1987, 52, 4202–4206.
Musicki, B., and Widlanski, T.S., *J. Org. Chem.,* 1987, 55, 4231–4233.
Tronchet, J.M.J., et al., *J. Carbohydrate Chem.,* 1991, 10(4), 723–728.
Mungall, W.S. and Kaiser, J.K., *J. Org. Chem.,* 1977, 42, 703–706.
Musicki and Widlanski, *Tetrahedron Letters,* 1991, 32, 1267–1270.
Ogilvie and Cormier, *Tetrahedron Letters,* 1985, 26, 4159–4162.
Huang, Z., et al., *J. of Cellular Biochemistry,* Abstracts, 20th Annual Meeting, CD209.
Coull, et al., *Tetrahedron Letters,* 1987, 28, 745–748.
Stirchak, et al., *Nucleic Acids Research,* 1989, 17, 6129–6134.
Mertes and Coats, *J. Med. Chem.,* 1969, 12:154.
Matteucci, et al., *J. Am. Chem. Soc.,* 1991, 113, 7767–7768.
Tittensor, J.R., *J. Chem. Soc. (C),* 1971., 2656–2662.
Veeneman, G.A., et al., *Tetrahedron,* 1991, 47, 1547–1562.
Cormier and Ogilvie, *Nucleic Acids Research,* 1988, 16, 4583–4595.
Schneider, K.C., and Benner, S.A., *Tetrahedron Letters,* 1990, 31, 335–338.
Trainor, et al., Third Chemical Congress of North America, Organic Chemistry, 1988, *The Design and Synthesis of Fluorescence-Tagged Dideoxynucleotides for Automated DNA Sequencing,* Canada, Jun. 5–10, 1988, Abstract No. ORGN 317.

Gait, M.J., et al., *J. Amer. Chem. Soc. Perkin I,* 1974, 1684.
Veeneman, G.A., et al., *Recueil des Trav. Chim,* 1990, 109:449.
Cohen, J.S., ed. *Oligonucleotides: Antisense Inhibitors of Gene Expression,* (CRC Press, Inc., Boca Raton, FL), 1989.
Wilson, D.B., *Ann Re. Biochem.* 1978, 47:933–965.
Miller, P.S., et al., *Biochmistry,* 1977, 16:1988–1996.
Marcus–Sekura, C.H., et al., *Nuc. Acids Res.,* 1987; 15:5749–5763.
Loke, S.K., et al., *Top. Microbiol. Immunol.,* 1988, 141:282:289.
Mazur, et al., *Tetrahedron,* 1984, 40:3949–3956.
Neumeyer, J.L., et al., *J. Org. Chem.,* 1973, 38:2291.
Matsuda, A., et al, *Nucleoside & Nucleotides,* 1990, 9:587.
Magid, et al., *Tett. Lets.,* 1990, 31:5595.
Kappler, et al., *Nucleic Acid Chemistry,* Part 4, Ed. L.B. Townsend and R.S. Tipson, Wiley–Interscience Publications, 1991, 240.
Bodenteich, M., et al., *Tetrahedron Letts.,* 1987, 28:5311.
Zon, G. and Stec, W.J., *Phosphorotioate Oligonucleotides, Oligonucleotides and Analogs A Practical Appraoch,* F. Eckstein, Ed., IRL Press, 1991, p. 87.
Nair, V. & Buenger, G.S., *Org. Prep. Procedures Int.,* 1990, 22:57.
Baud, et al., *Tet. Letts.,* 1990, 31:4437.
Verheyden, J.P.H. and Moffatt, J.G., *J. Org. Chem.,* 1970, 35:2119.
Rawson, T.E. and Webb, T.R., *Nucleosides and Nucleotides,* 1990, 9:89.

HETEROATOMIC OLIGONUCLEOSIDE LINKAGES

CROSS REFERENCE TO RELATED APPLICATIONS

This patent application is a continuation of application Ser. No. 07/903,160, filed on Jun. 24, 1992, now abandoned, which is a continuation-in-part of application PCT/US92/04294, filed on May 21, 1992. Application PCT/US92/04294 is a continuation-in-part of application Serial No. 07/703,619, filed on May 21, 1991 (now U.S. Pat. No. 5,378,825), which is a continuation-in-part of application Serial No. 07/566,836, filed on Aug. 13, 1990 (now U.S. Pat. No. 5,223,618), and application Ser. No. 07/558,663, filed on Jul. 27, 1990 (now U.S. Pat. No. 5,138,045). Each of these patent applications is assigned to the assignee of this patent application and are incorporated by reference herein.

FIELD OF THE INVENTION

This invention relates to the design, synthesis and application of nuclease resistant macromolecules that function as oligonucleotide mimics and are useful for therapeutics, diagnostics and as research reagents. The macromolecules have modified linkages in place of the phosphorodiester inter-sugar linkages found in wild type nucleic acids. The macromolecules are resistant to nuclease degradation and are capable of modulating the activity of DNA and RNA. Methods for synthesizing the macromolecules and for modulating the production of proteins, utilizing the macromolecules of the invention are also provided. Further provided are intermediate compositions useful in the synthesis of the macromolecules.

BACKGROUND OF THE INVENTION

It is well known that most of the bodily states in mammals, including most disease states, are effected by proteins. Such proteins, acting either directly or through their enzymatic functions, contribute in major proportion to many diseases in animals and man.

Classical therapeutics has generally focused upon interactions with such proteins in an effort to moderate their disease causing or disease potentiating functions. Recently, however, attempts have been made to moderate the actual production of such proteins by interactions with the molecules, i.e., intracellular RNA, that direct their synthesis. These interactions have involved the hybridization of complementary "antisense" oligonucleotides or certain analogs thereof to RNA. Hybridization is the sequence-specific hydrogen bonding of oligonucleotides or oligonucleotide analogs to RNA or single stranded DNA. By interfering with the production of proteins, it has been hoped to effect therapeutic results with maximum effect and minimal side effects. In the same way, oligonucleotide like macromolecules may modulate the production of proteins by an organism.

The pharmacological activity of antisense oligonucleotides and oligonucleotide analogs, like other therapeutics, depends on a number of factors that influence the effective concentration of these agents at specific intracellular targets. One important factor for oligonucleotides is their stability in the presence of nucleases. It is unlikely that unmodified oligonucleotides will be useful therapeutic agents because they are rapidly degraded by nucleases. Modifications of oligonucleotides to render them resistant to nucleases is therefore greatly desired.

Modifications of oligonucleotides to enhance nuclease resistance have generally taken place on the phosphorus atom of the sugar-phosphate backbone. Phosphorothioates, methyl phosphonates, phosphoramidates and phosphorotriesters have been reported to confer various levels of nuclease resistance. However, phosphate modified oligonucleotides have generally suffered from inferior hybridization properties. See Cohen, J. S., ed. Oligonucleotides: Antisense Inhibitors of Gene Expression, (CRC Press, Inc., Boca Raton Fla., 1989).

Another key factor is the ability of antisense compounds to traverse the plasma membrane of specific cells involved in the disease process. Cellular membranes consist of lipid-protein bilayers that are freely permeable to small, non-ionic, lipophilic compounds and inherently impermeable to most natural metabolites and therapeutic agents, see Wilson, D. B. *Ann. Rev. Biochem.* 47:933–965 (1978). The biological and antiviral effects of natural and modified oligonucleotides in cultured mammalian cells have been well documented. Thus, it appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs. For alkyl triester analogs, results have been reported by Miller, P. S., Braiterman, L. T. and Ts'O, P. O. P., *Biochemistry* 16:1988–1996 (1977). For methyl phosphonate analogs, results have been reported by Marcus-Sekura, C. H., Woerner, A. M., Shinozuka, K., Zon, G., and Quinman, G. V., *Nuc. Acids Res.* 15:5749–5763 (1987); Miller, P. S., McFarland, K. B., Hayerman, K. and Ts'O, P. O. P., *Biochemistry* 16:1988–1996 (1977); and Loke, S. K., Stein, C., Zhang, X. H. Avigan, M., Cohen, J. and Neckers, L. M. *Top. Microbiol. Immunol.* 141:282:289 (1988).

Often, modified oligonucleotides are less readily internalized than their natural counterparts. As a result, the activity of many previously available, modified antisense oligonucleotides has not been sufficient for practical therapeutic, research or diagnostic purposes. Two other serious deficiencies of prior modified oligonucleotides are inferior hybridization to intracellular RNA and the lack of a defined chemical or enzyme-mediated event to terminate essential RNA functions.

Modifications to enhance the effectiveness of antisense oligonucleotides and overcome these problems have taken many forms. These modifications include modifications of the heterocyclic base, modifications of the sugar, and modifications of sugar-phosphate backbone. Prior sugar-phosphate backbone modifications, particularly on the phosphorus atom, have effected various levels of resistance to nucleases. The ability of an antisense oligonucleotide to bind to specific DNA or RNA with fidelity is fundamental to antisense methodology. However, modified phosphorus oligonucleotides have generally suffered from inferior hybridization properties. Replacement of the phosphorus atom has been one approach to avoid the problems associated with modified phosphorous oligonucleotides. Certain modifications have been reported in which replacement of the phosphorus atom is effected. Matteucci, M., *Tetrahedron Letters* 31:2385–2388 (1990), reported replacement of the phosphorus atom with a methylene group. However, such replacement is limited by the difficulties associated with uniform insertion of a formacetal linkage throughout an oligonucleotide backbone. Cormier, et al., *Nucleic Acids Research* 16:4583–4594 (1988) reported the replacement of the phosphorus moiety with a diisopropylsilyl moiety. Stirchak, et al., *Journal of Organic Chemistry* 52:4202–4206 (1987) reported replacement of the phosphorus linkage by short homopolymers containing carbamate or morpholino linkages. Both of these replacements are limited by a lack of suitable synthetic methodology and the low solubility and weak hybridization properties of the resultant molecules. Mazur, et al., *Tetrahedron* 40:3949–3956 (1984) reported replacement of the phosphorus linkage with a phosphonic linkage. This replacement has not been developed beyond the synthesis of a homotrimer molecule. Goodchild, J., *Bioconjugate Chemistry* 1:165–187 (1990) reported replacement by ester linkages. However, ester linkages are enzymatically degraded by esterases and are therefore unsuitable as a replacement for the phosphate bond in antisense applications.

A recent publication by Tronchet, J. et. al, *J. Carbohydrate Chemistry,* 10:723 (1991) reported the use of an oxyimino intergylcosidic linkage between two monosaccharides to form a disaccharide. In forming this linkages, a first carbonyl sugar, either a hexose or a pentose, was reacted with a second O-aminohexose sugar.

The limitations of the available methods for modification of the phosphorus backbone of oligonucleotides has led to a continuing and long felt need for other modifications that might provide resistance to nucleases and satisfactory hybridization properties for antisense oligonucleotide diagnostics, therapeutics, and research.

OBJECTS OF THE INVENTION it is an object of the invention to provide macro-molecules that function as oligonucleotide mimics for use in antisense oligonucleotide diagnostics, research reagents, and therapeutics.

It is a further object of the invention to provide oligonucleotide-mimicking macromolecules that possess enhanced cellular uptake.

Another object of the invention is to provide oligonucleotide-mimicking macromolecules that have greater efficacy than unmodified antisense oligonucleotides.

It is yet another object of the invention to provide methods for synthesis and use of such oligonucleotide-mimicking macromolecules.

These and other objects shall become apparent to persons skilled in the arts to which this invention pertains given this specification and its appended claims.

BRIEF SUMMARY OF THE INVENTION

The present invention provides compositions that are useful for modulating the activity of an RNA or DNA molecule and that generally comprise oligonucleotide-mimicking macromolecules. The macromolecules are constructed from a plurality of linked nucleosides. In constructing these macromolecules, the phosphorodiester linkage of the sugar phosphate backbone found in wild type nucleic acids has been replaced with three and four atom linking groups. Such linking groups maintain a desired atomic spacing between the 3'-carbon of one nucleoside and the 4'-carbon of an adjacent nucleoside. The oligonucleotide-mimicking macromolecules of the invention comprise a selected linked sequence of nucleosides that are specifically hybridizable with a preselected nucleotide sequence of single stranded or double stranded DNA or RNA.

The oligonucleotide-mimicking macromolecules of the invention are synthesized conveniently, through solid state or solution methodology, to be complementary to or at least specifically hybridizable with a preselected nucleotide sequence of the RNA or DNA. Solid support synthesis is effected utilizing commercially available nucleic acid synthesizers. The use of such synthesizers is generally understood by persons of ordinary skill in the art as being effective in generating nearly any desired oligonucleotide or oligonucleotide mimic of reasonable length.

The oligonucleotide-mimicking macromolecules of the invention also can include nearly any modification known in the art to improve the properties of wild type oligonucleotides. In particular, the macromolecules can incorporate modifications known to increase nuclease resistance or hybridization.

In accordance with the present invention, novel macromolecules that function as antisense oligonucleotide mimics are provided to enhance cellular uptake, nuclease resistance, and hybridization properties and to provide a defined chemical or enzymatically mediated event to terminate essential RNA functions.

It has been found that certain oligonucleotidemimicking macromolecules can be useful in therapeutics and for other objects of this invention. At least a portion of the macromolecules of the invention has structure 1:

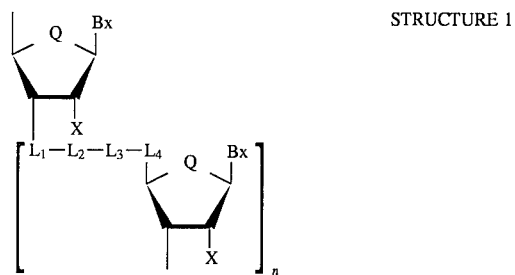

STRUCTURE 1 wherein one of $L_1$ or $L_2$ is O or S, and the other of $L_1$ or $L_2$ is N—R; and combined $L_3$ and $L_4$ are $CH_2$, or $L_3$ is $CH_2$ and $L_4$ is CR'R"; or one of $L_3$ or $L_4$ is O or S, and the other of $L_3$ or $L_4$ is N—R; and combined $L_1$ and $L_2$ are $CH_2$, or $L_2$ is $CH_2$ and $L_1$ is CR'R"; or one of $L_1$ and $L_4$ is O, S or N—R, and the other of $L_1$ and $L_4$ is CR'R"; and $L_2$ and $L_3$ are $CH_2$; or $L_1$, $L_2$, $L_3$ and $L_4$, together, are O—N=CH—$CH_2$ or $CH_2$—CH=N—O; or $L_1$ is O; $L_2$ is N; $L_3$ is $CH_2$; and $L_4$ is C or CH; and together with at least two additional carbon or hetero atoms, $L_2$, $L_3$ and $L_4$ form a 5 or 6 membered ring; or $L_1$ is C or CH; $L_2$ is $CH_2$; $L_3$ is N; and $L_4$ is O; and together with at least two additional carbon or hetero atoms, $L_1$, $L_2$ and $L_3$ form a 5 or 6 membered ring; and R is H; $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; a $^{14}C$ containing lower alkyl, lower alkenyl or lower alkynyl; $C_7$ to $C_{14}$ substituted or unsubstituted alkaryl or aralkyl; a $^{14}C$ containing $C_7$ to $C_{14}$ alkaryl or aralkyl; alicyclic; heterocyclic; a reporter molecule; an RNA cleaving group; a group for improving the pharmacokinetic properties of an oligonucleotide; or a group for improving the pharmacodynamic properties of an oligonucleotide;

R' and R" are H; or R' is H and R" is O—R; or combined R' and R" are =O;

X is H; O—R; S—R; NH—R; F, Cl; Br; CN; $CF_3$; $OCF_3$; OCN; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a reporter molecule; an RNA cleaving group; a group for improving the pharmacokinetic properties of an oligonucleotide; or a group for improving the pharmacodynamic properties of an oligonucleotide;

Q is O or $CH_2$;

n is an integer greater than 0; and

Bx is a variable heterocyclic base moiety.

The remainder of the molecule is composed of chemical functional groups that do not hinder, and preferably enhance, hybridization with RNA or single stranded or double stranded DNA.

In certain preferred embodiments, the macromolecules of structure 1 include macromolecules wherein one of $L_1$ or $L_2$ is O or S, and the other of $L_1$ or $L_2$ is N—R; and combined $L_3$ and $L_4$ are $CH_2$; or one of $L_3$ or $L_4$ is O or S, and the other of $L_3$ or $L_4$ is N—R; and combined $L_1$ and $L_2$ are $CH_2$.

Other preferred embodiments of the invention include macromolecules of structure 1 wherein one of $L_1$ and $L_4$ is O, S or N—R, and the other of $L_1$ and $L_4$ is CR'R'; and $L_2$ and $L_3$ are $CH_2$.

Further preferred embodiments of the invention include macromolecules of structure 1 wherein one of $L_1$ or $L_2$ is O or S, and the other of $L_1$ or $L_2$ is N—R; and $L_3$ is $CH_2$ and $L_4$ is CR'R"; or one of $L_3$ or $L_4$ is O or S, and the other of $L_3$ or $L_4$ is N—R; and $L_2$ is $CH_2$ and $L_1$ is CR'R".

Further preferred embodiments of the invention include macromolecules of structure 1 wherein $L_1$, $L_2$, $L_3$ and $L_4$, together, are O—N=CH—$CH_2$ or $CH_2$—CH=N—O.

Further preferred embodiments of the invention include macromolecules of structure 1 wherein $L_1$ is O; $L_2$ is N; $L_3$ is $CH_2$; and $L_4$ is C or CH; and together with at least two additional carbon or hetero atoms, $L_2$, $L_3$ and $L_4$ form a 5 or 6 membered ring; or $L_1$ is C or CH; $L_2$ is $CH_2$; $L_3$ is N; and $L_4$ is O; and together with at least two additional carbon or hetero atoms, $L_1$, $L_2$ and $L_3$ form a 5 or 6 membered ring.

In particularly preferred embodiments of the invention, Q of structure 1 is O. In accordance with other particularly preferred embodiments of the invention, X of structure 1 is H or OH. In accordance with other preferred embodiments of the invention the Bx group of individual nucleosides incorporated within structure 1 are independently selected from naturally occurring or synthetic purine and pyrimidine heterocyclic bases. Such heterocyclic bases include but are not limited to adenine, guanine, cytosine, thymine, uracil, 5-methylcytosine, hypoxanthine or 2-aminoadenine. Other such heterocyclic bases include 2-methylpurine, 2,6-diaminopurine, 6-mercaptopurine, 2,6-dimercaptopurine, 2-amino-6-mercaptopurine, 5-methylcytosine, 4-amino-2-mercaptopyrimidine, 2,4-dimercaptopyrimidine and 5-fluorocytosine.

Particularly preferred embodiments of the invention include macromolecules of structure 1 wherein $L_1$ is O or S, $L_2$ is N, $L_3$ is $CH_2$ and $L_4$ is $CH_2$ or CHOR, particularly where R is H. In accordance with other particularly preferred embodiments of the invention, $L_4$ is O or S, $L_3$ is N, $L_2$ is $CH_2$ and $L_1$ is $CH_2$ or CHOR, particularly where R is H. In accordance with even further particularly preferred embodiments of the invention, $L_2$ and $L_3$ both are $CH_2$ and one of $L_1$ or $L_4$ is N—R and the other is $CH_2$.

In preferred embodiments of the inventions, the oligonucleotide-mimicking macromolecules include from about 2 to about 50 nucleoside subunits (i.e., n=about 1–about 49).

The oligonucleotide-mimicking macromolecules of the invention preferably are included in a pharmaceutically acceptable carrier for therapeutic administration.

The substituent groups of the above referenced alkyl, alkenyl, alkynyl, alkaryl and aralkyl R groups include but are not necessary limited to halogen, hydroxyl, keto, carboxy, nitrates, nitrites, nitro, nitroso, nitrile, trifluoromethyl, O-alkyl, S-alkyl, NH-alkyl, amino, azido, sulfoxide, sulfone, sulfide, silyl, intercalators, conjugates, polyamines, polyamides, polyethylene glycols, polyethers, groups that enhance the pharmacodynamic properties of oligonucleotides, and groups that enhance the pharmacokinetic properties of oligonucleotides. One particularly preferred R group is $CF_3$. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine, and iodine. Groups that enhance the pharmacodynamic properties, in the context of this invention, include groups that improve oligonucleotide uptake, enhance oligonucleotide resistance to degradation, and/or strengthen sequence-specific hybridization with RNA. Groups that enhance the pharmacokinetic properties, in the context of this invention, include groups that improve oligonucleotide uptake, distribution, metabolism or excretion.

The invention further includes methods of modulating the production or activity of a protein in a cell system or an organism comprising contacting the cell system or organism with an oligonucleotide-mimicking macromolecule having structure 1.

The invention further includes methods of treating an organism having a disease characterized by the undesired production of a protein comprising contacting the organism with an oligonucleotide-mimicking macromolecule having structure 1.

The invention further includes methods of in vitro assaying a sequence-specific nucleic acid comprising contacting a test solution containing the nucleic acid with an oligonucleotide-mimicking macromolecule having structure 1.

The invention further includes nucleosidic precursors of the macromolecules of structure 1, the precursors having structure 2:

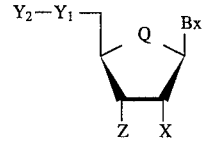

STRUCTURE 2 wherein $Y_1$ is O; $Y_2$ is H or R'"; and Z is aminooxy or phthalimidooxy; or $Y_1$ is $CH_2$, and $Y_2$ is aminooxy, alkylamino, aminooxyalkyl, alkenyl or oxoalkyl; and Z is H, OH, O—R'", amino methyleneamino or phthalimido;

R'" is a hydroxyl blocking group;

X is H or OH;

Q is $CH_2$ or O; and

Bx is a heterocyclic base moiety.

In certain preferred embodiments, $Y_1$ is $CH_2$; $Y_2$ is aminooxy, alkylamino, hydroxyalkyl, aminooxyalkyl, alkenyl or aldoalkyl; and Z is H, OH or O—R'". In other preferred embodiments, $Y_1$ is O, $Y_2$ is H and Z is aminoxy or phthalimido.

DETAILED DESCRIPTION OF THE INVENTION

The term "nucleoside" refers to a unit composed of a heterocyclic base and a sugar, generally a pentose sugar. In naturally occurring nucleosides, the heterocyclic base typically is guanine, adenine, cytosine, thymine or uracil. In naturally occurring nucleosides, the sugar is normally deoxyribose, i.e., erythro-pentofuranosyl, or ribose, i.e., ribopentofuranosyl. Synthetic sugars also are known, including arabino, xylo or lyxo pentofuranosyl sugars and hexose sugars. Throughout this specification, reference to the sugar portion of a nucleoside or other nucleic acid apecies shall be understood to refer to either a true sugar or to a species replacing the traditional sugar moiety of wild type nucleic acids. Additionally, reference to the heterocyclic base portion of a nucleoside or other nucleic acid species shall be understood to refer to either a natural, modified or synthetic base replacing one or more of the traditional base moiety of wild type nucleic acids. Moreover, reference to inter-sugar linkages shall be taken to include moieties serving to join the sugar or sugar substitute moiety together in the fashion of wild type nucleic acids.

The term "nucleotide" refers to a nucleoside having a phosphate group esterified to one of its 2', 3' or 5' sugar hydroxyl groups. The phosphate group normally is a monophosphate, a diphosphate or triphosphate.

The term "oligonucleotide" refers to a plurality of monophosphate nucleotide units that typically are formed in a specific sequence from naturally occurring bases and pentofuranosyl sugars joined by native phosphodiester bonds. A homo-oligonucleotide is formed from nucleotide units having the same heterocyclic base, i.e. poly(A). The term oligonucleotide generally refers to both naturally occurring and synthetic species formed from naturally occurring subunits.

The term "oligonucleotide analog" has been used in various published patent application specifications and other literature to refer to molecular species similarly to oligonucleotides but that have non-naturally occurring portions. This term has been used to identify oligonucleotide-like molecules that have altered sugar moieties, altered base moieties or altered inter-sugar linkages. Thus, the terminology oligonucleotide analog has been used to denote structures having altered inter-sugar linkages including phosphorothioate, methyl phosphonate, phosphotriester or phosphoramidate inter-nucleoside linkages used in place of phosphodiester inter-nucleoside linkages; purine and pyrimidine heterocyclic bases other than guanine, adenine, cytosine, thymine or uracil and sugars having other than the β pentofuranosyl configuration or sugars having substituent groups at their 2' position or substitutions for one or more of the hydrogen atoms. The term "modified oligonucleotide" also has been used in the literature to denote such structures.

"Oligonucleotide mimics" as the term is used in connection with this invention, refers to macromolecular moieties that function similarly to or "mimic" the function of oligonucleotides but, have non-naturally occurring intersugar linkages. Oligonucleotide mimics thus can have natural or altered or non-naturally occurring sugar moieties and natural or altered or non-naturally occurring base moieties in combination with non-naturally occurring inter-sugar linkages.

For the purposes of this invention, an oligonucleotide mimic having non-phosphodiester bonds, i.e. an altered inter-sugar linkage, can alternately be considered an "oligonucleoside" or an "oligonucleotide-mimicking macromolecule". The terms oligonucleoside or oligonucleotide-mimicking macromolecule thus refers to a plurality of joined nucleoside units connected by non-phosphate containing linking groups.

Additionally, the term "oligomers" is intended to encompass oligonucleotides, oligonucleotide analogs, oligonucleosides or oligonucleotide-mimicking macromolecules. Thus, in speaking of "oligomers" reference is made to a series of nucleosides or nucleoside analogs that are joined together via either natural phosphodiester bonds or via other linkages, including the linkages of this invention. Generally, the linkage is from the 3' carbon of one nucleoside to the 5' carbon of a second nucleoside. However, the term "oligomer" can also include other linkages such as a 2'→5' linkage or a 3'→4' linkage.

Antisense therapy is the use of oligonucleotides or other oligomers for the purpose of binding with complementary strands of RNA or DNA. After binding, the oligonucleotide and the RNA or DNA strand can be considered to be "duplexed" together in a manner analogous to native, double stranded DNA. The oligonucleotide strand and the RNA or DNA strand can be considered to be complementary strands in the same context as native double stranded DNA. In such complementary strands, the individual strands are positioned with respect to one another to allow Watson/Crick type hybridization of the heterocyclic bases of one strand to the heterocyclic bases of the opposing strand.

Antisense therapeutics can be practiced in a plethora of organisms ranging from unicellular prokaryotes and eukaryotes to multicellular eukaryotes. Any organism that utilizes DNA-RNA transcription or RNA-protein translation as a fundamental part of its hereditary, metabolic or cellular control is susceptible to antisense therapeutics and/or prophylactics. Seemingly diverse organisms such as bacteria, yeast, protozoa, algae, all plant and all higher animal forms, including warm-blooded animals, can be treated by antisense therapy. Further, since each of the cells of multicellular eukaryotes includes both DNA-RNA transcription and RNA-protein translation as an integral part of their cellular activity, antisense therapeutics and/or diagnostics can also be practiced on such cellular populations. Furthermore, many of the organelles, e.g. mitochondria and chloroplasts, of eukaryotic cells include transcription and translation mechanisms. Thus, single cells, cellular populations or organelles can also be included within the definition of organisms that are capable of being treated with antisense therapeutics or diagnostics. As used herein, therapeutics is meant to include the eradication of a disease state, killing of an organism, e.g. bacterial, protozoan or other infection, or control of erratic or harmful cellular growth or expression.

Prior antisense therapy utilizing "oligonucleotide analogs" is exemplified in the disclosures of the following United States and PCT patent applications: Ser. No. 463, 358, filed Jan. 11, 1990, entitled Compositions And Methods For Detecting And Modulating RNA Activity; Ser. No. 566,836, filed Aug. 13, 1990, entitled Novel Nucleoside Analogs; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides;, Ser. No. 558,806, filed Jul. 27, 1991, entitled Nuclease Resistant Pyrimidine Modified Oligonucleotides That Detect And Modulate Gene Expression; Ser. No. 703,619, filed May 21, 1991, entitled Backbone Modified Oligonucleotide Analogs; serial number PCT/US91/00243, filed Jan. 11, 1991, entitled Compositions and Methods For Detecting And Modulating RNA Activity; and patent application PCT/US91/01822, filed Mar. 19, 1991, entitled Reagents and Methods For Modulating Gene Expression Through RNA Mimicry; all assigned to the assignee of this invention. The disclosures of each of the above noted patent applications are herein incorporated by reference.

As is set forth in detail in the above-referenced United States and PCT patent applications, oligonucleotides and other oligomers have application in diagnostics, therapeutics, and as research reagents and kits. For therapeutic use, oligonucleotides or other oligomers would be administered to an animal, including humans, suffering from a disease state that is desirous to treat.

This invention is directed to certain macromolecules that function like oligonucleotides yet exhibit other useful properties. As is illustrated in the Examples and Schemes of this specification, the macromolecules are constructed from basic nucleoside units. These nucleoside units are joined by a linkage of the invention to form dimeric units. The dimeric units can be further extended to trimeric, tetrameric and other, higher order macromolecules by the addition of further nucleosides. The dimeric units (and/or the higher order units) can be linked via linkages other than those of the invention, as for instance, via a normal phosphodiester linkage, a phosphorothioate linkage, a phosphoramidate linkage, a phosphotriester linkage, a methyl or other alkylphosphonate linkage, a phosphorodithioate linkage or other linkage.

In certain embodiments, a single linkage is used to join nucleosides to form a macromolecule of the invention. For example, in Scheme XVIII below, m and r are 0, q is 1, and n and p are greater than 1. In other embodiments, two or more different linkages are used. For example, in Scheme XVIII, m and r are 0, q is 1, and n and p are greater than 1.

In other macromolecules of the invention the nucleoside are joined together in groups of two, three or more nucleoside that together form a unit. An activated phosphityl moiety is located at the 3' terminus of this unit and a hydroxyl moiety bearing a removable hydroxyl blocking group is located at the 5' terminus. On subsequent removal of the hydroxyl blocking group and reaction of the hydroxyl group with an activated phosphityl group, the units are then joined together via a normal phosphodiester, phosphorothioate or other phosphorus linkage. Thus a first unit (a group of two, three or more nucleosides linked together via a first linkage of the invention) and to a second unit (a group of two, three or more nucleosides linked together via the first linkage or via a second linkage of the invention) are connected together through a phosphate linkage. The macromolecule is elongated by the addition of further units of nucleosides (linked together via the first, a second or additional linkages of the invention) by joining these additional units to the existing linked units via further phosphorus linkages. In the examples and flow schemes shown below, units exemplified by compound 58 could be linked together or they could be linked to units of compounds 66, 72, 77, 81 or 85 or various combinations of these compounds could be linked together in various macromolecule structures. As is exemplified in Scheme XVIII below, in such macromolecules r is 0 or 1, m is a positive number, q is greater than 1, and n and p are positive numbers.

Scheme I illustrates certain abbreviations used for blocking groups in other of the Schemes. Scheme I further shows the synthesis of 3'-O-amino and 3'-O-methyleneamino nucleosides via a Mitsunobu reaction utilizing N-hydroxylphthalimide and methylhydrazine to generate an $—O—NH_2$ moiety on a sugar hydroxyl. The $—O—NH_2$ group can then be derivatized to a —O-methyleneamino moiety. These reactions are exemplified in Examples 1, 2, 3, 5 and 15.

The reactions of Examples 1, 2, 3 and 5 represent an improved synthesis of 3'-O—$NH_2$ nucleosides. In forming —O—$NH_2$ moieties on sugars, it is theoretically possible to displace a leaving group, as for instance a tosyl group, with hydroxylamine. However, Files, L. E., Winn, D. T., Sweger, R. W., Johnson, M. P., and Czarnik, *J. Am. Chem. Soc.*, 14:1493 (1992) have shown that such a displacement leads to a preponderance of —NHOH moieties and not to the desired —O—$NH_2$ moieties. Further, the reaction sequence of Examples 1, 2, 3 and 5 represents an improved synthesis compared to that illustrated in European Patent Application 0 381 335. The synthetic pathway of that patent application requires the use of a xylo nucleoside as the staring material. Xylo nucleosides are less readily obtainable than the ribonucleoside utilized in Examples 1, 2, 3 and 5.

Scheme II illustrates the conversion of a 4'-aldo nucleoside to a 5'-aldo nucleoside. This reaction is exemplified in Example 16. Scheme III illustrates the generation of a 5'-aldo methyl sugar. This is exemplified in Example 14. Scheme IV illustrates the formation of an 5'-iodo nucleoside, exemplified in Example 6. Similar methodology is used to generate an active iodo group on a terminal hydroxyl of a dimeric unit in Scheme X and Example 10. In Scheme IV, the iodo nucleoside is further derivatized to a 6'-aldo nucleoside via an allo substituted nucleoside. This is exemplified in Examples 31 and 32.

Scheme V illustrates a free radical reaction of a —O-methyleneamino nucleoside of Scheme 1 to a 5'-amino 5'-homo nucleoside. This is exemplified in Example 30. Scheme VI illustrates use of a Mitsunobu reaction on a 5'-homo nucleoside to synthesize an oxyamine homo nucleoside, i.e. a 6'-O—$NH_2$ 5'-homo nucleoside. This is exemplified in Examples 36, 37 and 38. Scheme VII illustrates N-alkylation of the amino moiety of a 6'-amino-5'-deoxy'5-homo nucleoside. This is exemplified in Examples 43, 44 and 45. Such N-alkylation is desirable where the amino moiety subsequently will be reacted with a thiol moiety. The N-alkylated product of such a reaction exhibits greater stability to acid than does the non-alkylated S—N bond. This is particularly useful in solid support synthesis wherein acid removal of trityl groups is commonly practiced. However, for other synthesis, such as solution synthesis, this may not be a concern.

Schemes VIII to XVII illustrate the use of the nucleosides of Schemes I to VII for the assembly of dimeric, trimeric and other, higher order oligonucleosides. In Scheme VIII, nucleosides 3 and 31 are joined via an acid catalyzed coupling reaction to form an —O-nitrilomethylidyne linkage between the respective two nucleosides. This is exemplified in Example 17. Dimeric oligonucleoside 32 can be reduced to an iminomethylene linkage that, in turn, can be alkylated to a (methylimino)methylene linkage, as exemplified in Example 18.

Scheme IX illustrates the joining of nucleoside 3 to nucleoside 5. This scheme is analogous to Scheme VIII with the exception that in Scheme IX a three atom linkage is created whereas in Scheme VIII a four atom linkage is created. Nucleosides 3 and 5 are joined in Step 1 to form an —O-nitrilo linkage that is reduced in Step 2 to an —O-imino linkage. Alkylation occurs in Step 3 to a —O-methylimino linkage, with final deblocking in Step 4. These steps are exemplified in Example 4. The alkylation reaction in Step 3 is accompanied by deblocking the t-butyldimethylsilyl protecting group at the 5' terminus of the dimer. Advantageous use of this deblocking reaction also is utilized in other Schemes. Deblocking of the t-butyldiphenylsilyl group used to protect the 3' terminus of the dimer is effected using tetra-n-butylammonium fluoride.

The alkylation step can be used to introduce other, useful, functional molecules on the macromolecule. Such useful functional molecules include but are not limited to reporter molecules, RNA cleaving groups, groups for improving the pharmacokinetic properties of an oligonucleotide, and groups for improving the pharmacodynamic properties of an oligonucleotide. Such molecules can be attached to or conjugated to the macromolecule via attachment to the nitrogen atom in the backbone linkage. Alternatively, such molecules can be attached to pendent groups extending from the 2' position of the sugar moiety of one or more of the nucleosides of the marcromolecules. Examples of such other useful functional groups are provided by U.S. patent application Ser. No. 782,374, filed Oct. 24, 1991, entitled Derivatized Oligonucleotides Having Improved Uptake & Other Properties, assigned to the same assignee as this application, herein incorporated by reference, and in other of the above-referenced patent .applications.

Scheme X illustrates a synthetic scheme utilized to prepare dimers, trimers, and other, higher order oligonucleosides having homogenous linkages between nucleosides. In this scheme, nucleosides 10 and 12 are linked to form an iminomethylene linkage as exemplified in Example 7. Advantageous use of the alkylating-5' terminus deblocking step of Scheme IX is effected to remove the blocking group at the 5' terminus of the dimeric oligonucleoside 14, as in Example 8. Using the iodination reaction of Scheme IV, the dimer is then converted to a 5' terminus iodo intermediate, as in Example 10. A further 3'-O-methyleneamino nucleosidic unit 10 then can be added to the dimer to form a trimer, as in Example 11, followed by deblocking and alkylation, as in Example 12. This reaction sequence can be repeated any number of times to form a higher order oligonucleoside. The oligonucleoside is deblocked at the 3' terminus, as is exemplified for the dimer in Example 9 or the tetramer in Example 13.

Scheme XI illustrates the use of an 1-O-alkyl sugar that is first linked to a nucleoside. Reduction followed by alkylation and deblocking yields an —O-(methylimino)methylene linkage joining the 1-O-alkyl sugar and the nucleoside, as exemplified by Example 19. This structure is then blocked at the 5' terminus, as exemplified by Example 20. The fully blocked, linked sugar-nucleoside structure is then subjected to glycosylation to add a heterocyclic base to the sugar moiety and thus form a dimeric nucleoside structure, as in Example 21. After glycosylation, removal of the 5' terminus blocking group and chromatographic separation of α and β anomers, as exemplified by Example 22, yields a dimer. This dimer can be further elongated as per the procedure of Scheme X. Examples 23, 34 and 25 exemplify the addition of an adenine, cytosine and guanine base to a thymidine-methyl sugar dimer to form T-A, T-C and T-G dimers in addition to the T-T dimer of Scheme X. Examples 26, 27 and 28 exemplify the formation of A-T, A-A, A-C, A-G, C-T, C-A, C-C, C-G, G-T, G-A, G-C and G-G dimers. Each may be further elongated as per the procedures of Scheme X.

Scheme XII illustrates a radical reaction that forms a linkage having a pendant hydroxyl moiety. This is exemplified in Example 33. The pendant OH group can be oxidized to an =O using Moffatt oxidization conditions. Alternatively, the pendant OH moiety can be cyclized to the nitrogen atom of the linkage to form either a five or a six membered heterocyclic ring. The formation of a linkage incorporating a six atom ring is exemplified in Example 34. A five atom ring would be formed utilizing condition analogous to those of Neumeyer, J. L. & Boyce, C. B., *J. Org. Chem.*, 38:2291 (1973) to add phosgene in the presence of a base such as triethylamine or diethylphenylamine in toluene at a temperature of about 60° to about 80° C.

Scheme XIII illustrates the formation of an iminooxymethylene linkage. Example 35 describes the preparation of the 5'-O-trityl protected xylo starting nucleoside and Example 39 describes the reaction of compound 50 with compound. 54 to form a dimeric unit. Continuing within Scheme XIII, to prepare dimeric units that can be used as solid support building blocks (Example 40), the backbone nitrogen atom is alkylated, followed by simultaneous removal of both the 5'-O-trityl and the 3'-O-(t-butyldiphenylsilyl) protecting groups with trifluoroacetic acid. The 5'-terminus hydroxyl group is blocked with dimethoxytriryl (Example 41), followed by forming an active phosphoramidate dimer (Example 42).

Scheme XIV illustrates the preparation of a thiol 2 intermediate and the use of that intermediate with an amino nucleoside to form a S-iminomethylene linkage (Example 45). As with the reactions of Scheme XIII, a dimeric unit having an active phosphoramidate moiety can be formed. This is exemplified by Examples 46 and 47.

Scheme XV illustrates the preparation of a nucleoside intermediate and coupling of that intermediate to a further nucleoside, as exemplified in Example 48, to form a nitrilo-1,2-ethanediyl linkage. This linkage can be reduced to an imino-1,2-ethanediyl linkage, as exemplified in Example 49. Further, in a manner similar to Schemes XIII and XIV, Scheme XV illustrates the preparation of an active phosphoramidate species, as exemplified in Examples 50, 51 and 52.

Scheme XVI illustrates the preparation of a 2' substituted nucleoside, as exemplified in Example 53, and conversion of that 2' substituted nucleoside to a further nucleoside having an active linkage forming moiety (Example 54). Linkage of this 2' substituted nucleoside to a further nucleoside (Example 55) is followed by conversion to an active phosphoramidate (Example 56). Substitution of the 2' position in a macromolecule of the invention, as noted above, is useful for the introduction of other molecules, including the introduction of reporter molecules, RNA cleaving groups, groups for improving the pharmacokinetic properties of an oligonucleotide, and groups for improving the pharmacodynamic properties of an oligonucleotide as well as other groups including but not limited to O, S and NH alkyl, aralkyl, aryl, heteroaryl, alkenyl, alkynyl and $^{14}$C containing derivatives of these groups, F, Cl, Br, CN, $CF_3$, $OCF_3$, OCN, $SOCH_3$, $SO_2CH_3$, $ONO_2$, $NO_2$, $N_3$, $NH_2$, heterocycloalkyl, heterocycloalkaryl, aminoalkylamino, polyalkylamino and substituted silyl.

Further illustrated in Scheme XVI is the preparation of a carbocyclic nucleoside (Example 57), joining of that carbocyclic nucleoside with a further nucleoside via a linkage of the invention (Example 58), and formation of an active phosphoramidate (Example 63). A further sequence of reactions are also illustrated in Scheme XVI, wherein a carbocyclic nucleoside is derivatized at its 2' positions (Example 60) and converted to a further nucleoside (Example 61). As with the other reactions of this scheme, a dimer is first formed (Example 62), and then derivatized with an active phosphoramidate (Example 63). The dimers of this scheme having a 3' phosphoramidite moiety are used as in schemes XIII, XIV and XV to link the oligonucleosides of the invention to other nucleosides via a phosphodiester, phosphorothioate or other similar phosphate based linkage.

Scheme XVII illustrates a further carbocyclic containing, dimeric nucleoside. Internucleoside conversion is exemplified in Examples 64 and 65, and formation of a dimeric structure is exemplified in Example 66. The dimeric structure of Scheme XVII shows a carbocyclic nucleoside as the 5' nucleoside of the dimer, while Scheme XVI shows a carbocyclic nucleoside as the 3' nucleoside of the dimer. Use of carbocyclic nucleosides for both nucleoside intermediates, in the manner as described for other of the reaction schemes, results in a dimer having a carbocyclic nucleoside at both the 3' and 5' locations.

Scheme XVIII illustrates generic structures that are prepared from the nucleosides and oligonucleoside of the previous schemes. Exemplary macromolecules of the invention are described for both solid support and solution phase synthesis in Example 68.

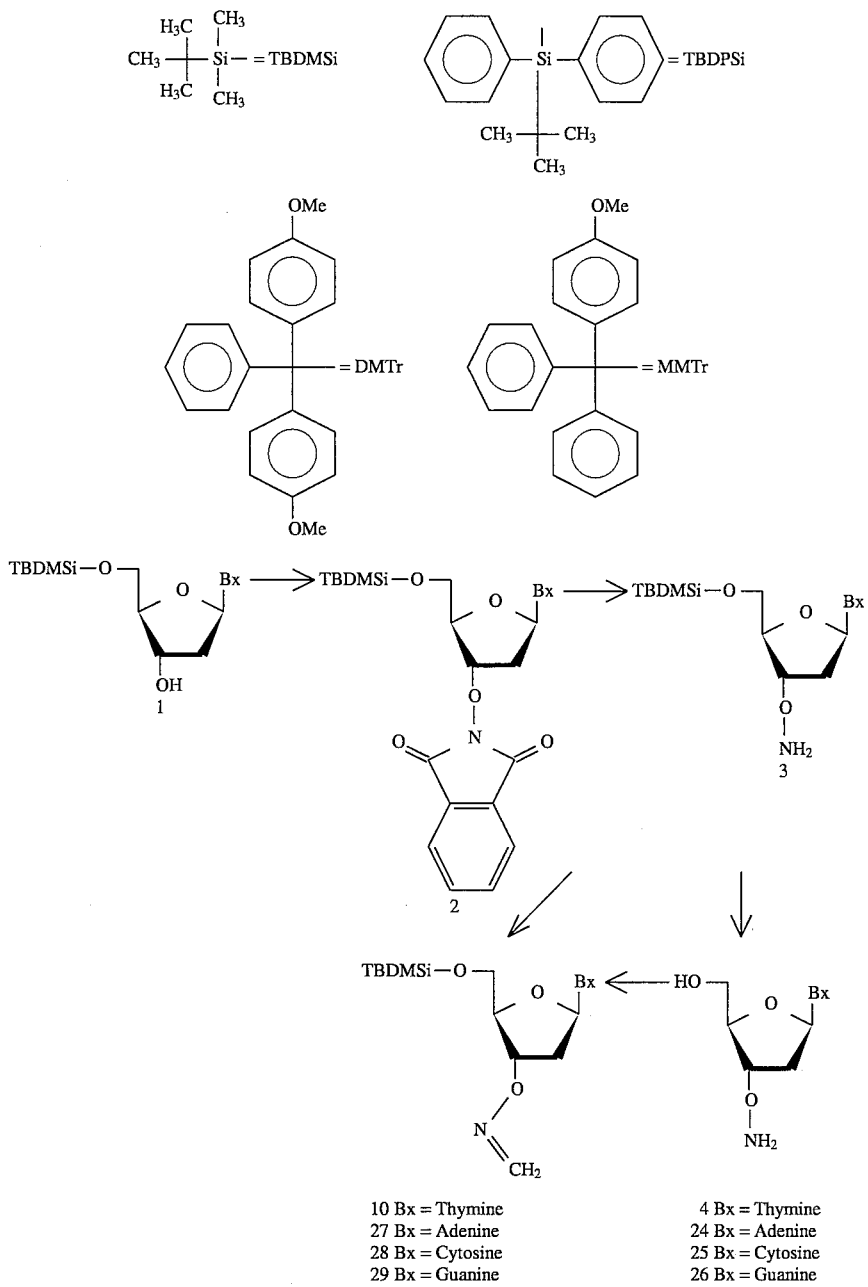

SCHEME I

SCHEME II
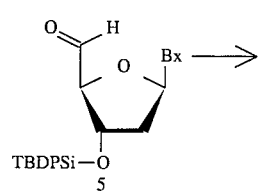
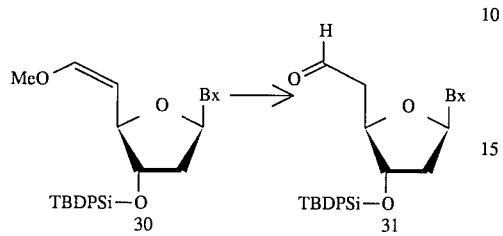
SCHEME III
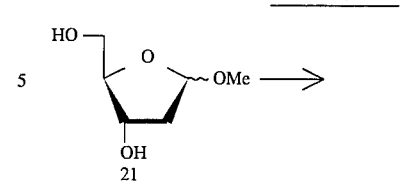
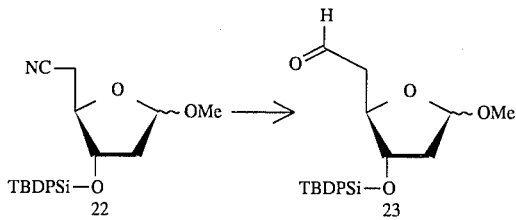
SCHEME IV
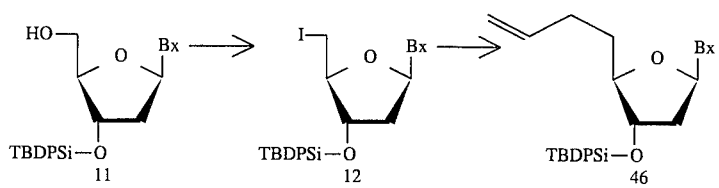
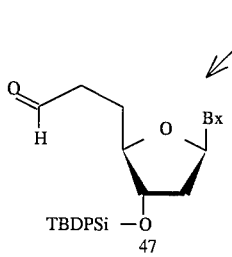
SCHEME V
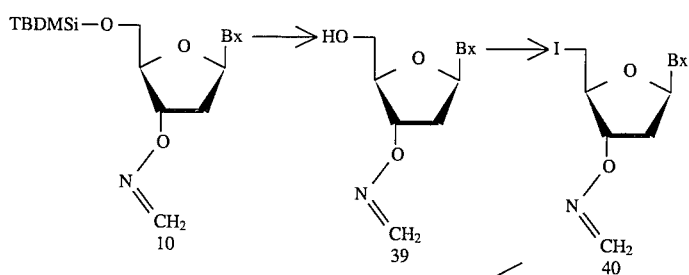

-continued
SCHEME V
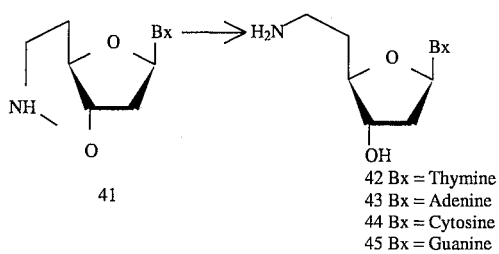
42 Bx = Thymine
43 Bx = Adenine
44 Bx = Cytosine
45 Bx = Guanine
SCHEME VI
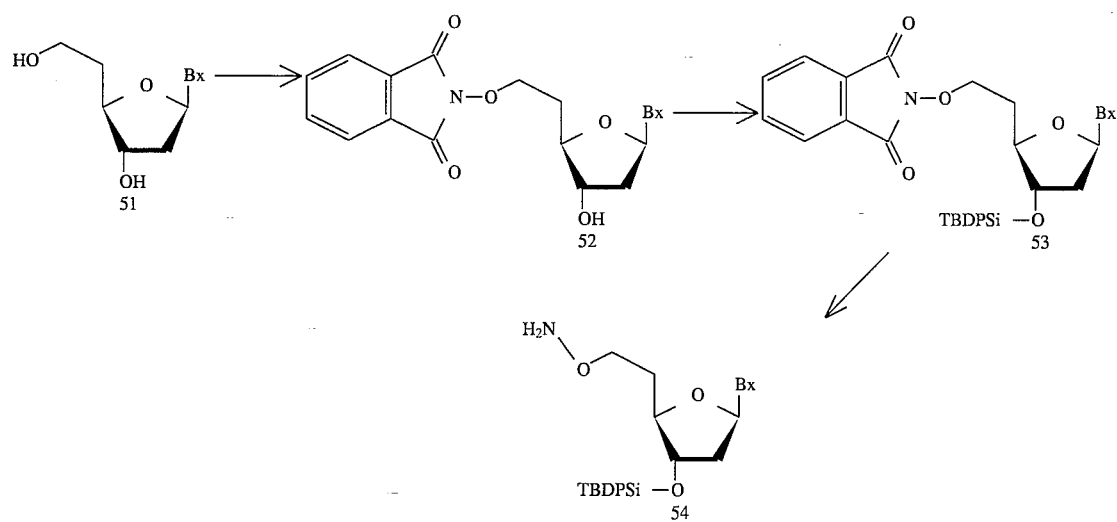
SCHEME VII
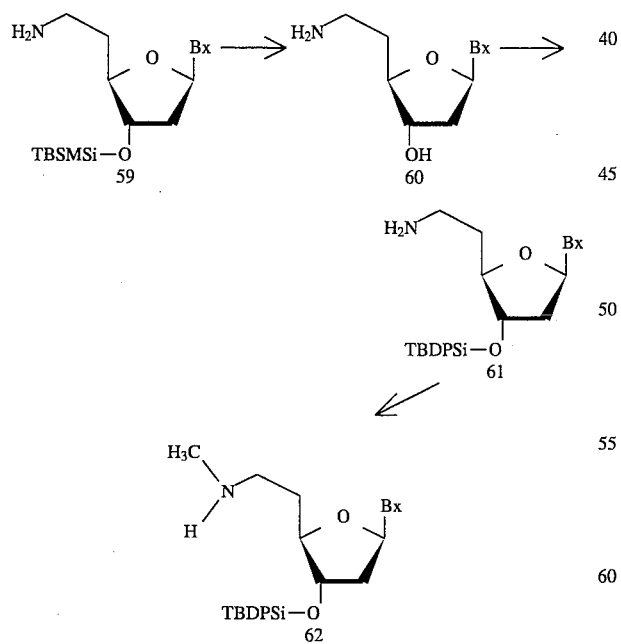
SCHEME VIII
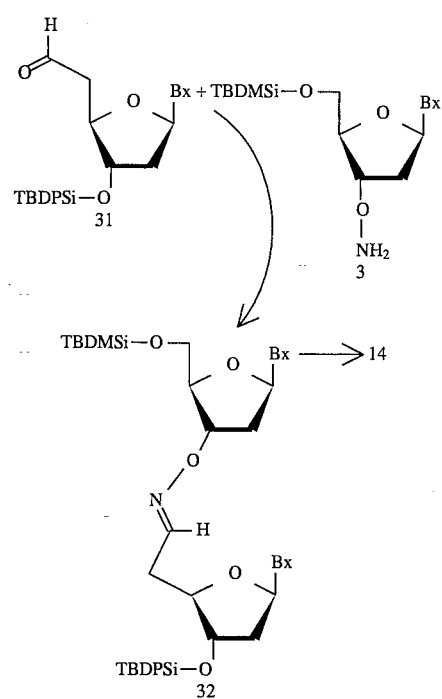

19
SCHEME IX
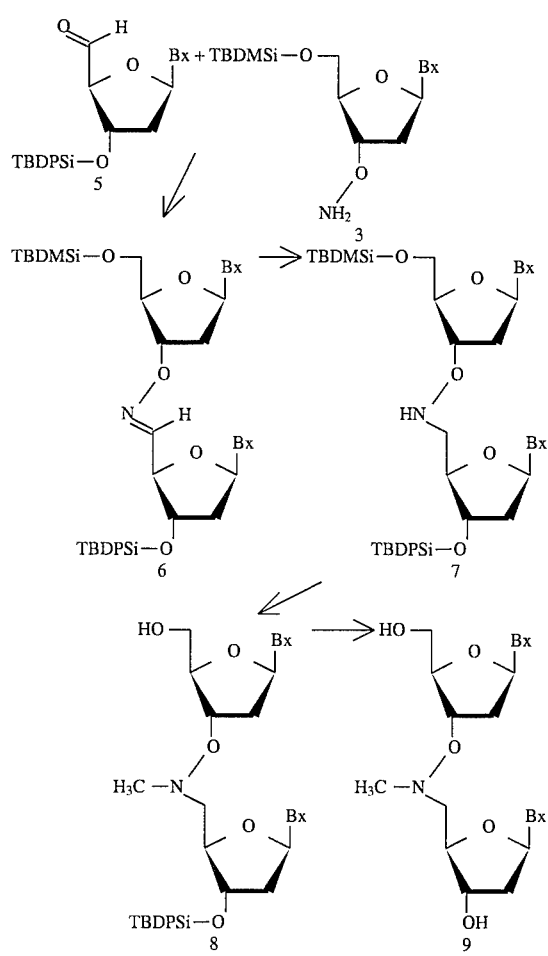
SCHEME X
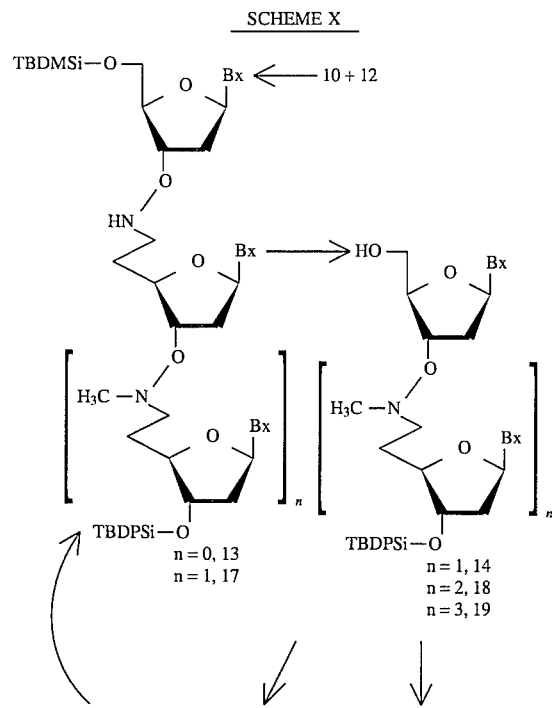
20
-continued
SCHEME X
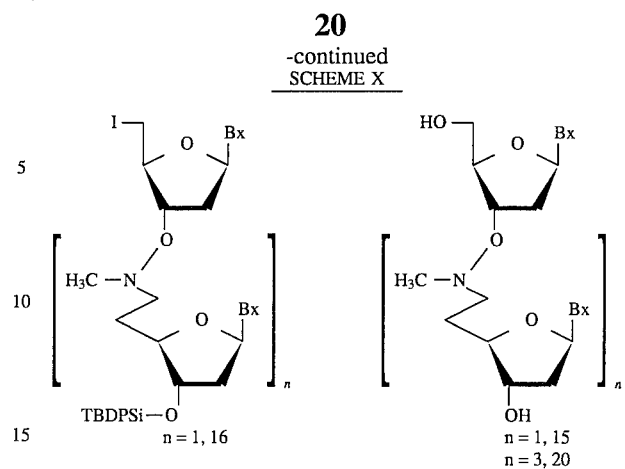
SCHEME XI

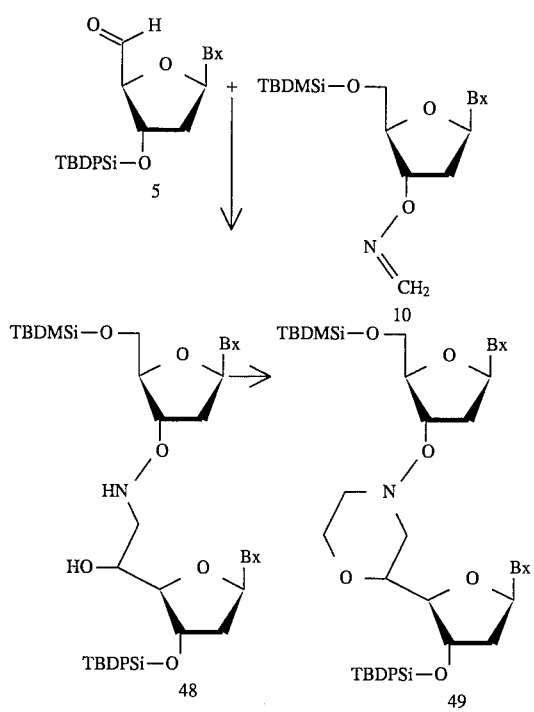
SCHEME XII
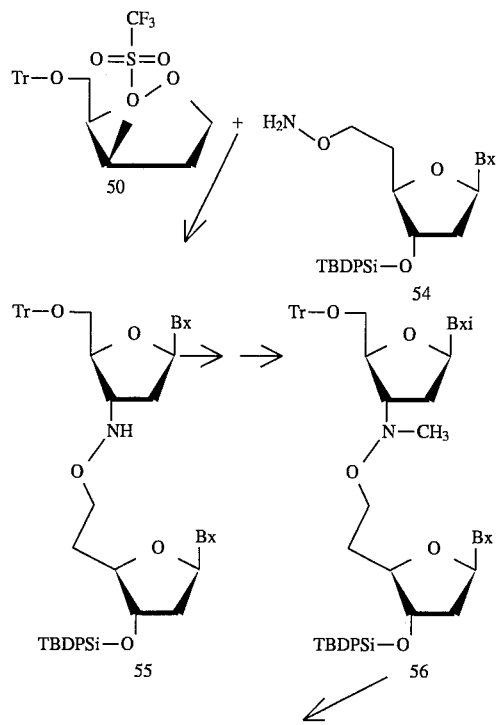
SCHEME XIII
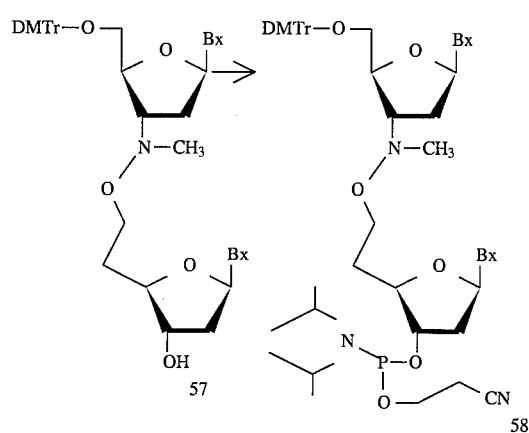
-continued
SCHEME XIII
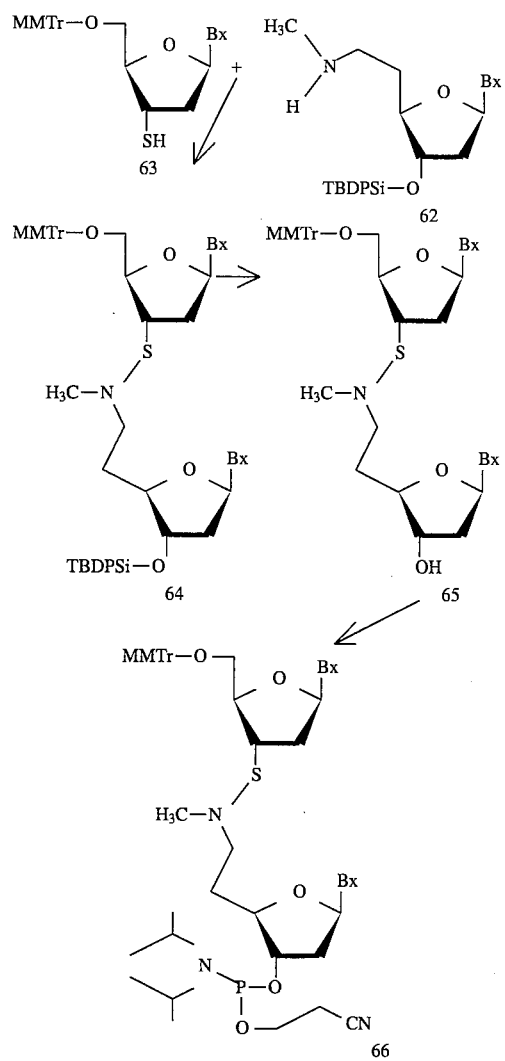
SCHEME XIV SCHEME XV
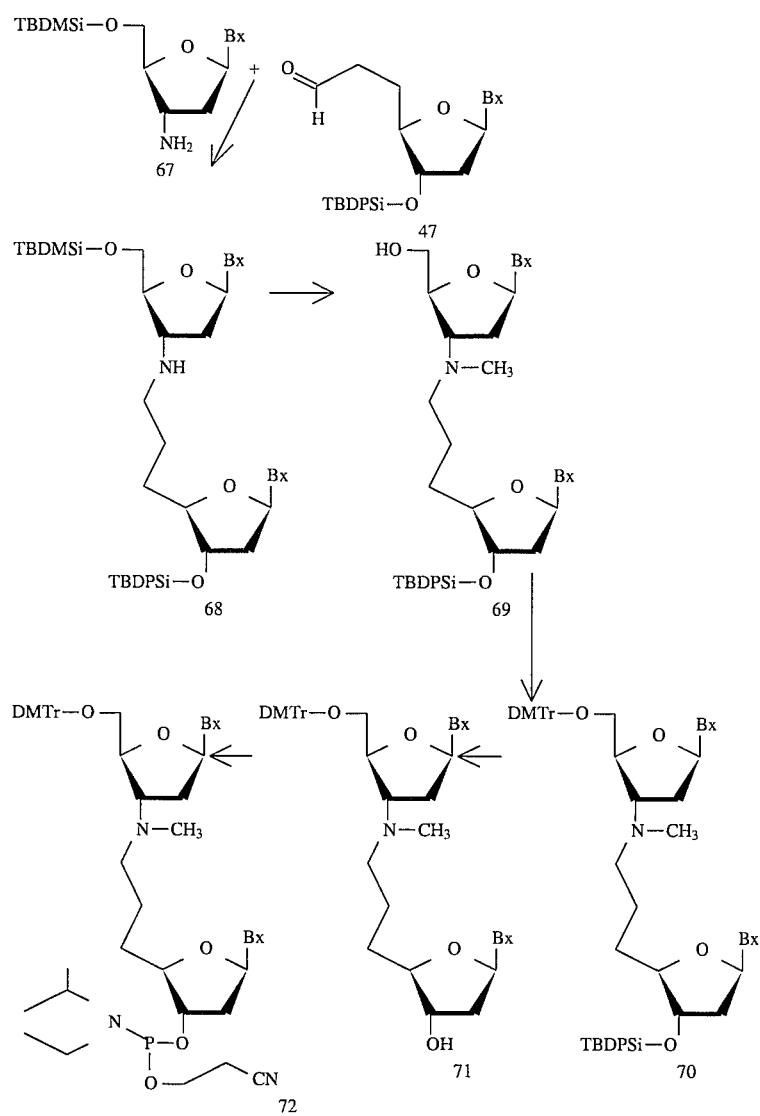
SCHEME XVI
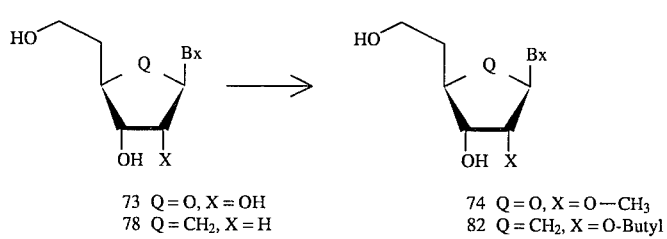
73  Q = O, X = OH
78  Q = CH₂, X = H
74  Q = O, X = O—CH₃
82  Q = CH₂, X = O-Butyl -continued
SCHEME XVI
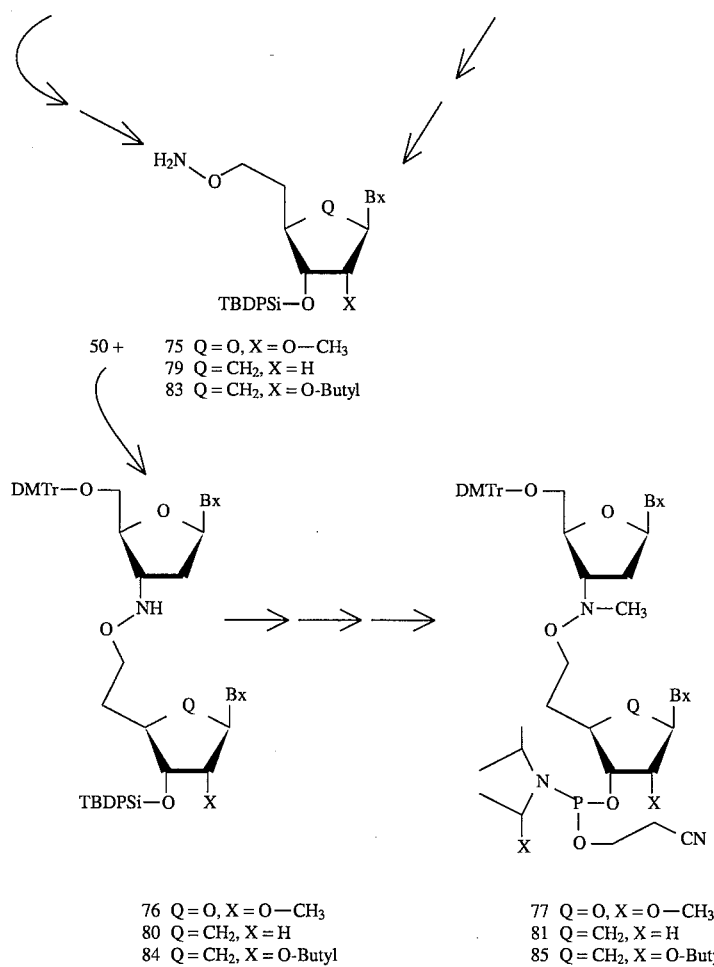
50 + 75 Q = O, X = O—CH₃
79 Q = CH₂, X = H
83 Q = CH₂, X = O-Butyl
76 Q = O, X = O—CH₃
80 Q = CH₂, X = H
84 Q = CH₂, X = O-Butyl
77 Q = O, X = O—CH₃
81 Q = CH₂, X = H
85 Q = CH₂, X = O-Butyl
SCHEME XVII
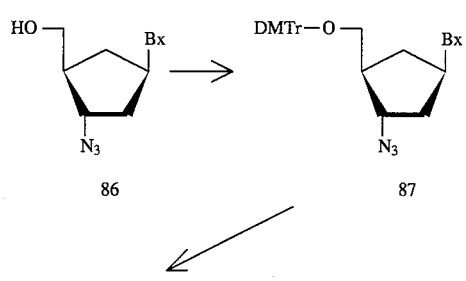
-continued
SCHEME XVII
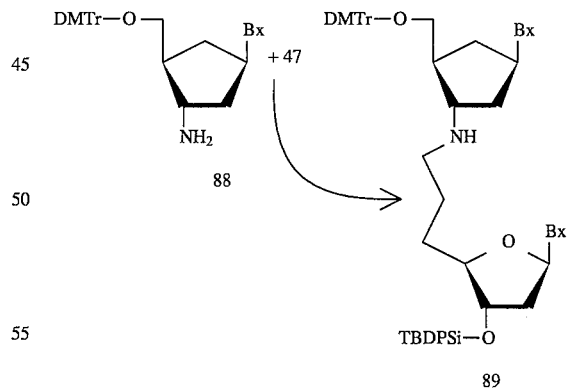

SCHEME XVIII

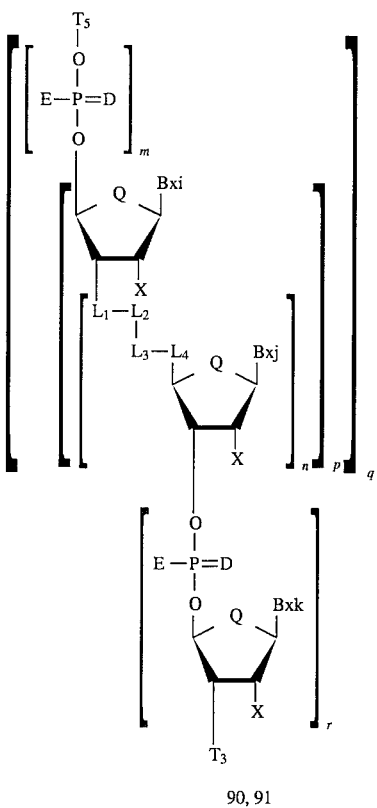

90, 91

EXAMPLE 1

5'-O-(t-Butyldimethylsilyl)-3'-O-Phthalimidothymidine, 2

To a solution of 5'-O-t-butyldimethylsilylthymidine [1, 21.36 g, 60 mmol, prepared according to the procedure of Nair, V., and Buenger, G. S., *Org. Prep. Procedures Int.*, 22:57 (1990) in dry THF (750 ml)], triphenylphosphine (17.28 g, 66 mmol) and N-hydroxyphthalimide (10.74 g, 66 mmol) were added. The solution was cooled to 0° C. and diisopropylazodicarboxylate (15.15 g, 75 mmol) was added dropwise over a period of 3 hr while stirring under nitrogen. The reaction mixture was then stirred at room temperature for 12 hr. The solution was evaporated and the residue was dissolved in $CH_2Cl_2$ (750 ml), extracted with sat. $NaHCO_3$ (200 ml), and water (200 ml), dried ($MgSO_4$), filtered and concentrated to furnish yellow oily residue. Silica gel column chromatography (100% hexanes, and then hexanes:$Et_2O$ gradient to 90% $Et_2O$) of the residue gave compound 2 as a colorless glass (18.68 g, 62%); $^1$H NMR ($CDCl_3$) δ0.05 [2s, 6, ($CH_3$)$_2$], 0.91 [s, 9, ($CH_3$)$_3$], 2.0 (s, 3, $CH_3$), 2.5–2.65 (m, 2, 2'$CH_2$), 4.05–4.2 (m, 2, 5'$CH_2$), 4.25–4.35 (m, 1, 4'$H$), 5.0 (m, 1, 3'$H$), 6.15 (m, 1, 1'$H$), 8.6 (br s, 1, N$H$), and aromatic protons.

Anal. Calcd. for $C_{24}H_{31}N_3O_7Si$: C, 57.46; H, 6.23; N, 8.37. found : C, 57.20; H, 6.26; N, 8.27.

EXAMPLE 2

3'-O-Amino-5'-O-(t-Butyldimethylsilyl)thymidine, 3

Cold methylhydrazine (1.6 ml, 30 mmol) was added to a stirred solution of 5'-O-(t-butyldimethylsilyl)-3'-O-phthalimidothymidine (2, 4.6 g, 9.18 mmol) in dry $CH_2Cl_2$ (60 ml) at 5°–10° C. After 10 minutes white precipitation of 1,2-dihydro-4-hydroxy-2-methyl-1-oxophthalizine occurred. The suspension was stirred at room temperature for 1 h. The suspension was filtered and precipitate washed with $CH_2Cl_2$ (2×20 ml). The combined filtrates were concentrated and the residue purified by silica gel column chromatography. Elution with $CH_2Cl_2$:MeOH (100:0→97:3, v/v) furnished the title compound (3.40 g, 100%) as white solid. Crystallization from $CH_2Cl_2$ gave white needles, m.p. 171° C.; $^1$H NMR ($CDCl_3$) δ0.05 [s, 6, ($CH_3$)$_2$], 0.90 [s, 9, ($CH_3$)$_3$], 2.22–2.58 (2m, 2, 2'$CH_2$), 3.9–4.08 (m, 3, 5'$CH_2$, and 3' $H$) 4.30 (m, 1, 4$H$) 5.5 (br s, 2, N$H_2$) 6.2 (m, 1, 1'$H$) 7.45 (s, 1, $C_6H$) 8.9 (br s, 1, N$H$).

Anal. Calcd. for $C_{16}H_{29}N_3O_5Si$: C, 51.72; H, 7.87; N, 11.32. found: C, 51.87, H, 7.81; N, 11.32.

EXAMPLE 3

3'-O-Aminothymidine, 4

3'-O-Amino-(t-butyldimethylsilyl)thymidine was deblocked with (Bu)$_4$NF/THF in standard way to furnish compound 4 (72%). Crystallized from ether/hexanes/ethanol as fine needles, mp 81° C. $^1$H NMR ($Me_2SO-d_6$) δ1.78 (s, 3, $CH_3$), 2.17 and 2.45 (2m, 2, 2'$CH_2$), 3.70 (m, 2, 5'$CH_2$), 3.88 (m, 1, 4'$H$), 4.16 (m, 1, 3'$H$), 4.8 (br s, 1, 5'O$H$), 6.05 (dd, 1, 1'$H$M), 6.2 (br s, 2 N$H_2$), 7.48 (s, 1, $C_6H$), and 11.24 (br s, 1, N$H$).

Anal. Calcd. for $C_{10}H_{15}N_3O_5$: C, 46.69; H, 5.87; N, 16.33; found: C, 46.55; H, 5.91; N, 16.21.

EXAMPLE 4

3'-O-Dephosphinico-3'-O-(Methylimino)thymidylyl-(3'→5')-5'-Deoxythymidine, 9

Step 1.

3'-O-Amino-5'-O-(t-butyldimethylsilyl)thyroidine (3, 1.85 g, 5 mmol), 3'-O-(t-butyldimethylsilyl)thyroidine-5'-aldehyde [5, 2.39 g, 5 mmol; freshly prepared by following the method of M. J. Camarasa, F. G. De las Heras, and M. J. Perez-Perez, *Nucleosides and Nucleotides*, 9:533 (1990)] and AcOH (0.25 ml) were stirred together in $CH_2Cl_2$ (50 ml) solution at room temperature for 2 h. The products were then concentrated under reduced pressure to give the intermediate oxime linked dimer, compound 6.

Step 2.

The residue obtained from Step 1 was dissolved in AcOH (25 ml). NaCNBH$_3$ (1.55 g, 25 mmol, in 3-portions) was added to the stirred AcOH solution at room temperature. The solution was stirred for 30 min to give the intermediate imine linked dimer, compound 7.

Step 3.

Aqueous HCHO (20%, 2 ml 66 mmol) and additional NaCNBH$_3$ (1.55 g, 25 mmol, in 3-portions) was added to the stirred reaction mixture of Step 2 at room temperature. After 2 h, the solution was diluted with EtOH (100 ml) , and resulting suspension was evaporated under reduced pressure. The residue was dissolved in $CH_2Cl_2$ (150 ml) and then washed successively with 0.1M HCl (100 ml), saturated aqueous $NaHCO_3$ (100 ml), and water (2×50 ml). The dried ($MgSO_4$) $CH_2Cl_2$ solution was evaporated to give crude methylated imine linked dimer 8.

Step 4.

The residue from Step 3 was dissolved in the THF (30 ml) and a solution of (Bu)$_4$NF (1M in THF, 10 ml) was added while stirring at room temperature. After 1 h, the reaction mixture was evaporated under reduced pressure and the residue was purified by short column chromatography. The appropriate fractions, which eluted with CH$_2$Cl$_2$:MeOH (8:2, v/v) were pooled and evaporated to give compound 9 as a foam (0.74 g, 30%). $^1$H NMR (Me$_2$SO-d$_6$) δ1.78 (s, 6, 2CH$_3$), 2.10 (m, 4, 2'CH$_2$), 2.5 (s, 3, N—CH$_3$), 2.8 (m, 2, 5'-N—CH$_2$), 3.6–4.08 (5m, 6, 5' CH$_2$, 4' CH, 3' CH), 4.75 and 5.3 (2 br s, 2, 3' and 5' OH), 6.02 (d, 1, 1'H), 6.1 (t, 1, 1'H), 7.4 and 7.45 (2s, 2, 2C$_6$H), 11.3 (br s, 2, NH).

EXAMPLE 5

5'-O-(t-Butyldimethylsilyl)-3'-Deoxy-3'-[(Methyleneamino)oxy]thymidine, 10

A solution of HCHO (20% aqueous, 1 ml) was added dropwise to a stirred solution of 3'-O-amino-5'-O-(t-butyldimethylsilyl)thymidine (3, 7.42 g, 20 mmol) in dry MeOH (400 ml) at room temperature. After 6 h, another portion of HCHO (20% aqueous, 1.5 ml) was added and stirring continued for 16 h. The resulting solution was evaporated under reduced pressure, and the residue was purified by chromatography on silica gel to give compound 10 (7.25 g, 95%) as clear foam. $^1$H NMR (CDCl$_3$) δ0.1 [s, 3, (CH$_3$)$_2$], 0.9 [s, 9, (CH$_3$)$_3$], 1.9 (s, 3, CH$_3$), 2.25–2.72 (m, 2, 2' CH$_2$), 3.85–4.15 (2m, 3, 5' CH$_2$, 4'H), 4.85 (m, 1, 3' H), 6.25 (dd, 1, 1'H), 6.5 and 6.95 (2d, 2, N=CH$_2$), 7.43 (s, 1, (6H), 9.2 (br s, 1 NH).

EXAMPLE 6

3'-O-(t-Butyldiphenylsilyl)-5'-Deoxy-5'-Iodothymidine 12

To a stirred solution of 3'-O-(t-butyldiphenylsilyl)thymidine [11, 10.0 g, 20.83 mmol, prepared according to the procedure of Koster, H. and Sinha, N. D., *Tet. Letts.*, 26:2641 (1982)] in dry DMF (375 ml) was added methyltriphenoxyphosphonium iodide (12.12 g, 30 mmol) under argon at room temperature. The solution was stirred for 16 h. The DMF was removed under reduced pressure and the residue was dissolved in CH$_2$Cl$_2$ (500 ml). The organic layer was washed with 20% aqueous Na$_2$S$_2$O$_3$ (200 ml), water (2×200 ml) and dried (MgSO$_4$). The solvent was evaporated and the residue was purified by silica gel chromatography. Elution with Et$_2$O: Hexanes (1:1, v/v), pooling of appropriate fractions and concentration furnished compound 12 as white power (7.87 g, 64%, mp 142° C.). Anal. Calcd. for C$_{26}$H$_{31}$N$_2$O$_4$SiI: C, 52.88; H, 5.29; N, 4.74; I, 21.33. Found: C,52.86; H, 5.21; N, 4.66; I, 21.54.

EXAMPLE 7

5'-O-(t-Butyldimethylsilyl)-3'-O-Dephosphinico-3'-O-(Iminomethylene)thymidylyl-(3'→5')-3'-O-(t-Butyldiphenylsilyl)-5'-Deoxythymidine, 13

A stirred solution of 5'-O-(t-butyldimethylsilyl)-3'-deoxy-3'-[(methyleneamino)oxy]thymidine (10, 1.62 g, 4.23 mmol), 3'-O-(t-butyldiphenylsilyl)-5'-deoxy-5'-iodothymidine (12, 2.5 g, 4.23 mmol), bis(trimethylstannyl)benzopinacolate [4.84 g, 8.46 mmol, prepared according to the method of Hillgartner, H; Neumann, W. P.; Schroeder, B., Liebigs *Ann. Chem.*, 586–599 (1975)] in dry benzene (9 ml) was carefully degassed 3-times (flushed with argon) and heated at 80° C. for 8 h. The reaction mixture was cooled and concentrated under reduced pressure and the residue was purified by silica gel chromatography. The appropriate fractions, which were eluted with CH$_2$Cl$_2$:MeOH (97:3, v/v), were pooled and concentrated to give dimeric oligonucleoside, compound 13 (1.25 g, 35%) as white foam. $^1$H NMR (CDCl$_3$) δ0.09 and 0.13 [2s, 6, (CH$_3$)$_2$], 0.89 and 1.06 [2s, 9, (CH$_3$)$_3$], 1.07 and 1.08 [2s, 9, (CH$_3$)$_3$], 1.87, and 1.90 (2s, 6, 2 CH$_3$), 5.74 (br s, 1, NH), 6.20–6.31 (2m, 2, 2 1'H), 6.88 (s, 1, C$_6$H), 10.33 and 10.36 (2 br s, 2, 2NH) and other protons.

EXAMPLE 8

3'-O-Dephosphinico-3'-O-[(Methylimino)methylene] thymidylyl-(3'→5')-3'-O-(t-Butyldiphenylsilyl)-5'-Deoxythymidine, 14

Method A

Compound 13 was treated as per the procedure of Step 3 of Example 4 to simultaneously N-alkylate the imino nitrogen and deblock the 5' silyl blocking group of the 5' nucleoside of the dimer to yield compound 14 as a foam. $^1$H NMR (CDCl$_3$) δ1.07 (s, 9, (CH$_3$)$_3$), 1.85 and 1.88 (2s, 6, 2C H$_3$), 2.56 (s, 3, N—CH$_3$), 4.77 (br s, 1, 5' OH), 6.1 and 6.2 (2m, 2, 1'H), 7.4 and 7.62 (2m, 10, Ph H), 9.05 (br s, 2, 2 N H), and other protons.

EXAMPLE 9

3'-O-Dephosphinico-3'-O-[(Methylimino)methylene] thymidylyl-(3'→5')-5'-Deoxythymidine, 15

The 3'-O-(t-butyldiphenylsilyl) blocking group of compound 14 is removed as per the procedure of Step 4 of Example 4 to yield the fully deblocked dimeric oligonucleoside, compound 15.

EXAMPLE 10

3'-O-Dephosphinico-3'-O-[(Methylimino)methylene] -5'-Iodo5'-Deoxythymidylyl-(3'→5')-3'-O-(t-Butyldiphenylsilyl)-5'-Deoxythymidine, 16

Compound 14 is treated as per the procedure of Example 6 to yield the title dimeric oligonucleoside, compound 16, having a reactive iodo functionality at the terminal 5' position and a blocking group remaining at the 3' position.

EXAMPLE 11

5'-O-(t-Butyldimethylsilyl)-3'-O-Dephosphinico-3'-O-(Iminomethylene)thymidylyl-(3'→5')-3'-O-Dephosphinico-3'-O-[(Methyimino)methylene]-5'-Deoxythymidylyl-(3'→5')-3'-O-(t-Butyldiphenylsilyl)-5'-Deoxythymidine, 17

Compound 16 is reacted with compound 10 utilizing the conditions of Example 7 to extend the oligonucleoside to yield the trimeric oligonucleoside, compound 17.

EXAMPLE 12

3'-O-Dephosphinico-3'-O-[(Methylimino)methylene] thymidylyl-(3'→5')-3'-O-Dephosphinico-3'-O-[(Methyimino)methylene]-5'-Deoxythymidylyl-(3'→5')-3'-O-(t-Butyldiphenylsilyl)-5'-Deoxythyroidine, 18

Compound 17 when reacted as per the conditions of Example 8 will undergo N-alkylation to the trimeric oligonucleoside and will be deblock at the 5' position to yield compound 18, wherein n=2.

EXAMPLE 13

3'-O-Dephosphinico-3'-O-[(Methylimino)methylene]
thymidylyl-(3'→5')-3'-O-Dephosphinico-3'-O-[(Me-
thyimino)methylene]-5'-Deoxythymidylyl-(3'→5')-
3'-O-Dephosphinico-3'-O-[(Methyimino)methylene]-
5'-Deoxythymidylyl-(3'→5')-5'-Deoxythymidine, 20

The sequence of Examples 10, 11 and 12 is repeated for the addition of a further nucleoside to extend the oligonucleoside to a tetramer, compound 19. The tetrameric oligonucleoside 19 is then treated as per the procedure of Example 9 to remove the terminal 3' silyl blocking group yielding the fully deblocked tetrameric oligonucleoside, compound 20.

EXAMPLE 14

Methyl3-O-(t-Butyldiphenylsilyl)-2,5-Dideoxy-5-C-
Formyl-α/β-D-erythro-Pentofuranoside, 23

2-Deoxy-D-ribose, 21, was modified to methyl 2-deoxy-a/β-D-erythro-pentofuranoside (prepared according to the method of M. S. Motawai and E. B. Pedersen, Liebigs Ann. Chem. 1990, 599–602), which on selective tosylation followed by 3-O-silylation gave methyl 3-O-(t-butyldimethylsilyl)-2-deoxy-5-O-tosyl-α/β-D-erythro-pentofuranoside in overall 70% yield. The latter compound on iodination followed by cyanation gave the corresponding 5-C-cyano intermediate compound 22, as a syrup. $^1$H NMR (CDCl$_3$) δ1.05 (s, 9, (C$\underline{H}_3$)$_3$), 1.9–2.38 (m, 4, 2 C$\underline{H}_2$), 3.3 and 3.4 (2s, 3, OC$\underline{H}_3$), 3.98–4.30 (3m, 2, 3, 4-C$\underline{H}$), 4.95 and 5.05 (2m, 1, 1$\underline{H}$), 7.4 and 7.7 (2m, 10, Ph $\underline{H}$). IR (neat) 2253 cm$^{-1}$ (C$\underline{H}_2$ C$\underline{N}$)]. Compound 22 (stored at 0° C. without any degradation) was reduced(DIBAL-H) freshly every time as and when the title compound 23 was required.

EXAMPLE 15

5'-O-(t-Butyldimethylsilyl)-2',3'-Dideoxy-3'[(Methyleneamino)oxy]adenosine, 27;5'-O-(t-Butyldimethylsilyl)-2',3'-Dideoxy-3'-[(Methyleneamino)oxy]cytidine, 28; and 5'-O-(t-Butyldimethylsilyl)-2',3'-Dideoxy-3'-[(Methyleneamino)oxy]guanosine, 29

3'-O-Amino-2'-deoxyadenosine, compound 24, 3'-O-amino-2'-deoxycytidine, compound 25, and 3'-O-amino-2'-deoxyguanosine, compound 26, prepared as per the procedures of European Patent Application 0 381 335 or in a manner analogous to the preparation of compound 4 by the procedure of Example 3 above, are blocked at their 5' position with a t-butyldimethylsilyl group according to the procedure of Nair, V., and Buenger, G. S., Org. Prep. Procedures Int., 22:57 (1990) to give the corresponding 3'-O-amino-5'-(t-butyldimethylsilyl)-2'-deoxyadenosine, 3'-O-amino-5'-(t-butyldimethylsilyl)-2'-deoxycytidine and 3'-O-amino-5'-(t-butyldimethylsilyl)-2'-deoxyguanosine nucleoside intermediates. Treatment of the blocked intermediate as per the procedure of Example 5 or as per the procedure of Preparation example 4 of European Patent Application 0 381 335 gives the corresponding 5'-O-(t-butyldimethylsilyl)-2',3'-dideoxy-3'-[(methyleneamino)oxy]adenosine, compound 27; 5'-O-(t-butyldimethylsilyl)-2',3'-dideoxy-3'-[(methyleneamino)oxy]cytidine, compound 28; and 5'-O-(t-butyldimethylsilyl)-2',3'-dideoxy-3'-[(methyleneamino)oxy]guanosine, compound 29.

EXAMPLE 16

3'-O-(t-Butyldiphenylsilyl)thymidine-6'-
Aldehyde, 31

The title compound is prepared by homologation of the above described 3'-O-(t-butyldimethylsilyl)thymidine-5'-aldehyde (compound 5) utilizing the procedure of Barton, D. H. R. et al., Tet. Letts., 30:4969 (1989). The 5'-aidehyde, compound 5, is treated via a Witig reaction with (methoxymethylidene)triphenylphosphate. The resulting enol ether, compound 30, is hydrolyzed with Hg(OAc)$_2$, KI, H$_2$O and THF according to the procedure of Nicolaou, K. C., et al., J. Am. Chem. Soc., 102:1404 (1980) to furnish the compound 31.

EXAMPLE 17

5'-O-(t-Butyldimethylsilyl)-3'-O-Dephosphinico-3'-
O-(Nitrilomethylidyne)thymidylyl-(3'→5')-3'-O-
(t-Butyldiphenylsilyl)-5'-Deoxythymidine, 32

The title compound is prepared by reaction of compound 31 and compound 3 in the manner of Example 4, Step 1 to furnish the dimeric oligonucleoside having an oxime backbone.

EXAMPLE 18

3'-O-Dephosphinico-3'-O-[(Methylimino)methylene]
thymidylyl-(3'→5')-3'-O-(t-Butyldiphenylsilyl)-5'-
Deoxythymidine, 14

Method B

Compound 32 when treated as per the procedure of Steps 2 and 3 of Example 4 will also yield compound 14.

EXAMPLE 19

Methyl 3'-O-Dephosphinico-3'-O-[(Methyimino)methylene]thymidylyl-(3'→5)-3-O-(t-Butyldiphenylsilyl)-2,5-Dideoxy-α/β-D-erythro-Pentofuranoside, 33

Compound 23 and compound 3 are linked utilizing the procedure of Example 4, Steps 1 to couple the sugar and the nucleoside via an oxime linkage. The resulting oxime linkage is then reduced utilizing the procedure of Example 4, Step 2 to an iminomethylene linkage and this linkage, in turn, when N-alkylated via the procedure of Example 4, Step 3 will yield compound 33.

EXAMPLE 20

Acetyl 5'-O-Benzoyl-3'-O-Dephosphinico-3'-O-
[(Methyimino)methylene]thymidylyl-(3'→5)-3-O-
(t-Butyldiphenylsilyl)-2,5-Dideoxy-α/β-D-erythro-
Pentofuranoside, 34

Compound 33 will be treated with benzoyl chloride according to the procedure of Jenkins et al., Synthetic Procedures in Nucleic Acid Chemistry, Zorbach and Tipson, Ed., Vol. 1, John Wiley & Sons, Pg. 149, to benzoylate the free 5'-hydroxyl of compound 33 which is hydrolyzed and acylated in situ according to the procedure of Baud et. al, Tet. Letts., 31:4437 (1990) to yield compound 34.

EXAMPLE 21

5'-Benzoyl-3'-O-Dephosphinico-3'-O-[(Methylimino)methylene]thymidylyl-(3'→5')-3'-O-(t-Butyldiphenylsilyl)-5'-Deoxythymidine, 35

Compound 34 is reacted with silylated thymine as per the procedure of Baud, et al., *Tetrahedron Letters*, 31:4437 (1990) utilizing dibenzo-18-crown-6 and potassium iodide in acetonitrile-toluene to yield 5'-O-benzoyl-3'-O-dephosphinico-3'-O-[(methylimino)methylene]thymidylyl-(3'→5')-3'-O-(t-butyldiphenylsilyl)-5'-deoxythymidine, compound 35 as an anomeric mixture.

EXAMPLE 22

3'-O-Dephosphinico-3'-O-[(Methylimino)methylene]thymidylyl-(3'→5')-3'-O-(t-Butyldiphenylsilyl)-5'-Deoxythymidine, 14

Method C

Compound 35 when treated with methanolic ammonia will also yield compound 14. Further treatment as per the procedure of Example 9 will yield the fully deblocked dimer, from which anomerically pure compound 15 will be isolated by chromatography.

EXAMPLE 23

3'-O-Dephosphinico-3'-O-[(Methylimino)methylene]thymidylyl-(3'→5')-3'-O-(t-Butyldiphenylsilyl)-5'-Deoxyadenosine, 36

Compound 34 is reacted with silylated adenine as per the procedure of Baud, et al., *Tetrahedron Letters*, 31:4437 (1990) utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)methylene]thymidylyl-(3'→5')-3'-O-(t-butyldiphenylsilyl)-5'-deoxyadenosine, 36.

EXAMPLE 24

3'-O-Dephosphinico-3'-O-[(Methylimino)methylene]thymidylyl-(3'→5')-3'-O-(t-Butyldiphenylsilyl)-5'-Deoxycytidine 37

Compound 34 is reacted with silylated cytosine as per the procedure of Baud, et al., *Tetrahedron Letters*, 31:4437 (1990) utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)methylene]thymidylyl-(3'→5')-3'-O-(t-butyldiphenylsilyl)-5'-deoxycytidine, 37.

EXAMPLE 25

3'-O-Dephosphinico-3'-O-[(Methylimino)methylene]thymidylyl-(3'→5')-3'-O-(t-Butyldiphenylsilyl)-5'-Deoxyguanosine 38

Compound 34 is reacted with silylated guanine as per the procedure of Baud, et al., *Tetrahedron Letters*, 31:4437 (1990) utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)methylene]thymidylyl-(3'→5')-3'-O-(t-butyldiphenylsilyl)-5'-deoxyguanosine, 38.

EXAMPLE 26

A-(3'→5')-T; A-(3'→5')-A; A-(3→'5')-C; and A-(3'→5')-G 3'-Dephosphinico-3'-(Methylimino)methylene Linked Dimers In a manner analogous to the procedures of Examples 19 and 20, the 5'-(t-butyldimethylsilyl)-3'-O-aminoadenosine intermediate of Example 15 will be reacted with compound 3 to yield a linked nucleoside-sugar compound equivalent to compound 34 wherein Bxi is adenine. The linked nucleosidesugar intermediate will then be reacted as per the procedures of Examples 21, 23, 24 and 25 to yield the A-T, A-A, A-C and A-G dimers, respectively, of a structure equivalent to that of compound 14 where Bxi is adenine and Bxj is thymine, adenine, cytosine and guanine, respectively.

EXAMPLE 27

C-(3'→5')-T; C-(3'→5')-A; C-(3'→5')-C; and C-(3'→5')-G 3'-Dephosphinico-3'-(Methylimino)methylene Linked Dimers In a manner analogous to the procedures of Examples 19 and 20, the 5'-(t-butyldimethylsilyl).-3'-O-aminocytidine intermediate of Example 15 will be reacted with compound 3 to yield a linked nucleoside-sugar compound equivalent to compound 34 wherein Bxi is cytidine. The linked nucleoside-sugar intermediate will then be reacted as per the procedures of Examples 21, 23, 24 and 25 to yield the C-T, C-A, C-C and C-G dimers, respectively, of a structure equivalent to that of compound 14 where Bxi is cytosine and Bxj is thymine, adeninc, cytosine and guanine, respectively.

EXAMPLE 28

G-(3'→5')-T; G-(3'→5')-A; G-(3'→5')-C; and G-(3'→5')-G 3'-Dephosphinico-3'-(Methylimino)methylene Linked Dimers In a manner analogous to the procedures of Examples 19 and 20, the 5'-(t-butyldimethylsilyl)-3'-O-aminoguanosine intermediate of Example 15 will be reacted with compound 3 to yield a linked nucleoside-sugar compound equivalent to compound 34 wherein Bxi is guanine. The linked nucleoside-sugar intermediate will then be reacted as per the procedures of Examples 21, 23, 24 and 25 to yield the G-T, G-A, G-C and G-G dimers, respectively, of a structure equivalent to that of compound 14 where Bxi is guanine and Bxj is thymine, adeninc, cytosine and guanine, respectively.

EXAMPLE 29

Trimeric, Tetrameric, Pentameric, Hexameric And Other Higher Order Oligonucleosides Having a Selected Nucleoside Sequence The dimers of Examples 21, 23, 24, 25, 26, 27 and 28 are extended by reaction with the 5'-(t-butyldimethylsilyl)-3'-deoxy-3'-[(methyleneamino)oxy] nucleosides, compounds 10, 27, 28 and 29, of Examples 5 and 15 to form trimers utilizing the looping sequence of reactions of Examples 10, 11 and 12. Iteration of this reaction sequence loop adds a further nucleoside to the growing oligonucleoside per each iteration of the reaction sequence loop. The reaction sequence loop of Examples 10, 11 and 12 is repeated "n" number of times to extend the oligonucleoside to the desired "n+1" length. The final 3'-blocked oligonucleoside when treated as per the procedure of Example 9 to remove the terminal 3'-O-(t-butyldiphenylsilyl) blocking group will yield the fully deblocked oligonucleoside of the selected nucleoside sequence and length.

EXAMPLE 30

6'-Amino-6'-Deoxy-5'-Homothymidine, 42;
6'-Amino-2',6'-Dideoxy-5'-Homoadenosine, 43;
6'-Amino-2',6'-Dideoxy-5'-Homocytidine, 44; and
6'-Amino-2',6'-Dideoxy-5'-Homoguanosine, 45 (Via
An Intramolecular Free Radical Reaction)

Deblocking of compound 10 is effected by treatment with $Bu_4NF$ in THF. The resulting compound 39 (also reported in Preparation example 4 of European Patent application 0 381 335 A1) will be iodinated upon treatment with methyltriphenoxyphosphonium iodide as per the procedure of Verheyden, J. P. H. and Moffatt, J. G., *J. Org. Chem.*, 35:2119 (1970) to furnish 5'-deoxy-5'-iodo-3'-O-methyleneaminothymidine, compound 40. Compound 40 when subjected to an intramolecular free radical reaction according to the procedure of Curran, D. P., Radical Addition Reactions, *In Comprehensive Organic Synthesis*: Trost, B. M. and Fleming, I., Eds., vol. 4, p 715–832, Pergamon Press, Oxford (1991), will give the corresponding 3'-O-isoxazolidinethymidine, compound 41 which on DIBAL-H reduction will yield 6'-amino-5'-homothymidine, compound 42 [the 3'-(t-butyldimethylsilyl) derivative of this compound is reported in Rawson, T. E. and Webb, T. R., *Nucleosides & Nucleotides*, 9:89 (1990)].

When reacted in a like manner compounds 27, 28 and 29 will give 6'-amino-5'-homoadenosine, compound 43; 6'-amino-5'-homocytidine, compound 44; and 6'-amino-5'-homoguanosine, compound 45.

EXAMPLE 31

3'-O-(t-Butyldiphenylsilyl)-5'-Deoxy-5'-C-Allylthymidine 46

A stirred solution of 3'-O-(t-butyldiphenylsilyl)-5'-deoxy-5'-iododthymidine (12, 1.77 g, 3 mmol), allytributyltin (2.97 g, 9 mmol) and AIBN (0.54 g, 3.3 mmol) in dry toluene (30 ml) was degassed completely and heated at 65° C. for 6 hr. The solution was cooled and concentrated under vacuo. The residue was purified by silica gel column chromatography and on elution with hexanes:EtOAc (1:1, v/v) furnished the title compound as homogeneous material. Appropriate fractions were pooled and evaporated to furnish 46, 0.75 g of a white foam, 50% yield. The structure was confirmed by $^1H$ NMR.

EXAMPLE 32

3'-O-(t-Butyldiphenylsilyl)-5-Deoxy-7'-C-Aldehydothymidine 47

A solution of 46 (1 mmol), $OsO_4$ (0.1 mmol) and nmethylmorpholine oxide (2 mmol) in diethyl ether (4 ml) and water (2 ml) are stirred for 18 hr at room temperature. A solution of $NaIO_4$ (3 ml) is added and the solution further stirred for 12 hr. The aqueous layer is extracted with diethyl ether. Evaporation of the organic layer will give the crude aldehyde 47.

EXAMPLE 33

5'-O-(t-Butyldimethylsilyl)-3'-O-Dephosphinico-3'-O-(Iminomethylene)thymidylyl-(3'→5')-3'-O-(t-Butyldiphenylsilyl)-5'-Deoxy-5'-Hydroxythymidine, 48

Utilizing the procedure of Hanamoto, T. and Inanaga, J., *Tet. Letts.*, 32:3555 (1991), $SmI_2$ (0.1 mmol) in THF (3 ml) is added to a mixture of compound 5 and compound 10 in HMPA (0.5 ml) with stirring. The mixture will be stirred at room temperature for about 15 mins to form the adduct (as detected by the fading color). The solvent will be removed and the residue purified by column chromatography to give the dimeric oligonucleoside 48.

EXAMPLE 34

3'-O-Dephosphinico-3'-O-[N-(Morpholin-2-yl)]thymidylyl-(3'→4')-3'-O-(t-Butyldiphenylsilyl)-5'-Deoxy-5'-Demethylenethymidine, 49

Utilizing the modification of Lim, M.-I. and Pan, Y.-G., *Book of Abstracts*, 203 ACS national Meeting, San Francisco, Calif.., Apr. 5–10, 1992, of the procedure of Hill, J. and Ramage, G. R. J., *J. Chem. Soc.*, 3709 (1964), the dimeric oligonucleoside of Example 33 (compound 48, 1 equiv.) will be treated with chloroacetyl chloride in acetone to form an adduct with the amino group of the linkage. Further treatment with $K_2CO_3$ (1.2 equiv.) in DMSO at elevated temperature will cyclize the adduct to the hydroxyl group of the linkage to form a 5-oxomorpholino adduct with the linkage. The oxomorpholino adduct is then reduced with $BH_3$-THF under reflux to yield the dimer linked via an —O—[N-(morpholin-2-yl)]-linkage, compound 49.

EXAMPLE 35

N3-Benztoyl-1-(5'-O-Dimethoxytrityl-3'-O-Trifluoromethylsulfonyl-threo-Pentofuranosyl)thymine, 50

The method of Horwitz, J. P. et al., *J. Org. Chem.*, 29:2076 (1964) will be utilized to prepare the title compound with substitution of the trifluoromethanesulfonic anhydride/pyridine (−50° C. to 0° C.) reaction conditions of Fleet, G. W. J. et al., *Tetrahedron*, 44:625 (1988) for the methylsulfonic anhydride conditions of Horwitz et al.

EXAMPLE 36

6'-O-Phthalimido-5'-Homothymidine, 52

To a stirred mixture of 5'-homothymidine [Etzold, G., Kowollik, G., and Langen, R., *Chemical Communications*, pg 422 (1968)] (51, 1.28. g, 5 mmol), N-hydroxyphthalimide (1.09 g, 6.6 mmol) and triphenylphosphine (1.75 g, 6.6 mmol) in dry DMF (25 ml) will be added diisopropylazodicarboxylate (1.5 ml, 7.5 mmol) over a period of 30 min at 0° C. The stirring is continued for 12 hr at room temperature. The solvent is evaporated under vacuo and the residue is washed with diethyl ether (2×50 ml). The residue will then be suspended in hot EtOH (50 ml), cooled and filtered to give the title compound 52.5

EXAMPLE 37

6'-O-Phthalimido-3'-O-(t-Butyldiphenylsilyl)-Homothymidine 53

Compound 52 will be treated with t-butyldiphenylchlorosilane in pyridine and imidazole in a standard manner to afford the title compound 53.

EXAMPLE 38

6'-O-Amino-3'-O-(t-Butyldiphenylsilyl)-5'-Homothymidine, 54

To a stirred solution of compound 53 in dry $CH_2Cl_2$ is added methylhydrazine (3 mmol) under anhydrous conditions at room temperature. The solution is stirred for 12 hr, cooled (0° C.) and filtered. The precipitate will be washed with $CH_2Cl_2$ and the combined filtrates will be concentrated. The residue is purified by flash column chromatography (silica gel, 20 g). Elution with $CH_2Cl_2$:MeOH, 9:1, v/v) will furnish the title compound 54.

EXAMPLE 39

3'-De(oxophosphinico)-3'-(Iminooxymethylene)-5'-Tritylthymidylyl-(3'→5')-3'-O-(t-Butyldiphenylsilyl)-5'-Deoxythymidine, 55

6'-O-Amino-3'-O-(t-butyldiphenylsilyl)-5'-homothymidine, 54, is converted to the corresponding urethane with ethyl chloroformate ($CH_2Cl_2$-saturated $NaHCO_3$) utilizing the stereospecific conditions of Yang, D., Kim, S.-H. and Kahne, D., *J. Am. Chem. Soc.*, 113:4715 (1991). The residue of this reaction will then be stirred in $CH_2Cl_2$ with compound 50. The products are then concentrated in vacuo to yield the dimeric oligonucleoside, compound 55.

EXAMPLE 40

3'-De(oxophosphinico)-3'-[Methyl(iminooxymethylene)]-5'-Tritylthymidylyl-(3'→5')-3'-O-(t-Butyldiphenylsilyl)-5'-Deoxythymidine, 56

Compound 55 will be N-alkylated as per the conditions of Step 3 of Example 4 to yield the N-alkylate iminooxymethylene linked dimeric oligonucleoside 56.

EXAMPLE 41

3'-De(oxophosphinico)-3'-[Methyl(iminooxymethylene)]-5'-Dimethoxytritylthymidylyl-(3'→5')-5'-Deoxythymidine, 57

The 5'-O-trityl and the 3'-O-(t-butyldiphenylsilyl) protecting groups of compound 56 will be removed by treatment with trifluoroacetic acid and the residue dimethoxytritylated as per the procedure of Sproat, B. S. and Lamond, A. I., 2'-O-Methyloligoribonucleotides: synthesis and applications, Oligonucleotides and Analogs A Practical Approach, F. Eckstein Ed., IRL Press, pg. 55 (1991), to give the title compound.

EXAMPLE 42

3'-De(oxophosphinico)-3'-[Methyl(iminooxymethylene)]-5'-Dimethoxytritylthymidylyl-(3'→5')-3'-[(β-Cyanoethoxy)-N-(diisopropyl)phosphiryl]-5'-Deoxythymidine, 58

Compound 57 (1.89 mmol) will be dissolved in anhydrous dichloromethane under an argon atmosphere. Diisopropylethylamine (0.82 ml, 4.66 mmol) is added and the reaction mixture cooled to ice temperature. Chloro(diisopropylamino)-β-cyanoethoxyphosphine (0.88 ml, 4.03 mmol) is added to the reaction mixture and the reaction mixture is allowed to warm to 20° C. and stirred for 3 hr. Ethylacetate (80 ml) and triethylamine (1 ml) are added and the solution is washed with brine solution three times (3×25 ml). The organic phase is separated and dried over magnesium sulfate. After filtration of the solids the solvent is evaporated in vacuo at 20° C. to an oil that will then be purified by column chromatography using silica and a solvent such as hexane-ethyl acetatetriethylamine (50:40:1) as eluent. The fractions are then evaporated in vacuo and the residue will be further evaporated with anhydrous pyridine (20 ml) in vacuo (1 torr) at 26° C. in the presence of sodium hydroxide for 24 hr to yield the title compound 58.

EXAMPLE 43

5'-Amino-5'-Homothymidine, 60

5'-Amino-3'-O-(t-butyldimethylsilyl)-5'-homothymidine 59 is prepared as per Rawson, T. E., and Webb, T. R., *Nucleosides & Nucleotides*, 9:89 (1990). The t-butyldimethylsilyl group will be removed as per the procedure of Step 4 of Example 4 to give the title compound.

EXAMPLE 44

5'-Methylamino-3'-O-(t-Butyldiphenylsilyl)-5'-Homothymidine, 62

Compound 60 is t-butyldiphenylsilated as per the procedure of 37 to give 5'-Amino-3'-O-(t-butyldiphenylsilyl)-5'-homothymidine, compound 61, which will then be treated as per the procedure of Step 3 of Example 4 alkylate the 5'-amino group to yield the title compound 62.

EXAMPLE 45

3'-Dephosphinico-3'-S-[(Methylimino)methylene]-5'-Monomethoxytrityl-3'-Thiothymidylyl-(3'→5')-3'-(t-Butyldiphenylsilyl)-5'-Deoxythymidine, 64

5'-Methylamino-3'-O-(t-butyldiphenylsilyl)-5'-homothymidine 62 (1 mmol) will be added to aqueous sodium hypochloride (4 mmol) to furnish a chloramide intermediate. The chloramide intermediate is cooled (0° C.) and treated with 5'-O-monomethoxytrity-3'-thiothymidine (0.9 mmol), compound 63, prepared as per Cosstick, R. and Vyle, J. S., *Nucleic Acids Res.*, 18: 829 (1990). The reaction mixture is worked up utilizing the procedure of Barton, D. H. R. et al., *J. Org. Chem.*, 56:6702 (1991) and the residue will be purified by chromatography to give the title compound 64.

EXAMPLE 46

3'-Dephosphinico-3'-S-[(Methylimino)methylene]-
5'-Monomethoxytrityl-3'-Thiothymidylyl-(3'→5')-5'-
Deoxythymidine, 65

Compound 64 will be deblocked at the terminal 3' position utilizing the as per the procedure of Step 4 of Example 4 to give compound 65.

EXAMPLE 47

3'-Dephosphinico-3'-S-[(Methylimino)methylene]-
5'-Monomethoxytrityl-3'-Thiothymidylyl-(3'→5')-3'
[(β-Cyanoethoxy)-N-(diisopropyl)phosphortityl]-5'-
Deoxythymidine 66

Compound 65 will be phosphitylated as per the procedure of Example 42 to give the title compound 66.

EXAMPLE 48

5'-O-(t-Butyldimethylsilyl)-3'-De(oxyphosphinico)-
3'-(Imino-1,2-Ethanediyl)thymidylyl-(3'→5')3'-O-(t-
Butyldiphenylsilyl)-5'-Deoxythymidine, 68

3'-Amino'-5'-O-(t-butyldimethylsilyl)-3'-deoxythymidine, compound 67, prepared according to Matsuda, A., Satoh, M. and Ueda, T., *Nucleoside & Nucleotides*, 9:587 (1990) will be reductively coupled with compound 47 in the presence of a catalytic amount of acid as per the procedure of Magid et. al, *Tett. Lets.*, 31:5595 (1990), to yield the Schiff's base intermediate that is reduced in situ to give the amino linkage of the title compound 68.

EXAMPLE 49

3'-De(oxyphosphinico)-3'-[(Methylimino)-1,2-
Ethanediyl]thymidylyl-(3'→5')-3'-O-(t-Butyldiphenylsilyl)-5'-Deoxythymidine, 69

Compound 68 will be methylated and deblocked at the 5' position as per the procedure of Step 3 of Example 4 to yield the N-alkylated 5'-deblocked dimer, compound 69.

EXAMPLE 50

3'-De(oxyphosphinico)-5'-Dimethoxytrityl-3'-[(Methylimino)-1,2-Ethanediyl]thymidylyl-(3'→5')-3'-O-
(t-Butyldiphenylsilyl)-5'-Deoxythymidine, 70

Compound 69 will be dimethoxytritylated as per the procedure of Sproat, B. S. and Lamond, A. I., 2'-O-Methyloligoribonucleotides: synthesis and applications, Oligonucleotides and Analogs A Practical Approach, F. Eckstein Ed., IRL Press, pg. 55 (1991).

EXAMPLE 51

3'-De(oxyphosphinico)-5'-Dimethoxytrityl-3'-[(Methylimino)-1,2-Ethanediyl]thymidylyl-(3'→5')-5'-
Deoxythymidine, 71

The dimethoxytritylated intermediate, compound 70 when deblocked at the 3' terminus as per the procedure of Step 4 of Example 4 will give compound 71.

EXAMPLE 52

3'-De(oxyphosphinico)-5'-Dimethoxytrityl-3'-[(Methylimino)-1,2-Ethanediyl]thymidylyl-(3'→5')-3'-
[(S-Cyanoethoxy)-N-(diisopropyl)phosphiryl]-5'-
Deoxythymidine, 72

Compound 71 will be phosphitylated as per the procedure of Example 42 to give the title compound 72.

EXAMPLE 53

2'-O-Methylhomoadenosine, 74

Homoadenosine, 73, prepared as per the procedure of Kappler, F. and Hampton, A., *Nucleic Acid Chemistry*, Part 4, Ed. L. B. Townsend and R. S. Tipson, Wiley-Interscience Publication, pg. 240 (1991), will be blocked across its 3' and 5' hydroxyl groups with a TIPS, i.e. tetraisopropylsilyl, blocking group followed by alkylation as per the procedures described in United States patent applications 566,977, filed Aug. 13, 1990 and PCT/US91/05720, filed Aug. 12, 1991. Removal of the TIPS group with tetra-n-butylammonium fluoride as per the procedure of Step 4 of Example 4 will yield the title compound 74.

EXAMPLE 54

6'-O-Amino-3'-O-(t-Butyldiphenylsilyl)-5'-Homoadenosine, 75

Compound 74 will be treated as per the procedures of Examples 36, 37 and 38 to yield the title compound 75.

EXAMPLE 55

3'-De(oxophosphinico)-3'-(Iminooxymethylene)-5'-
Dimethoxytritylthymidylyl-(3'→5')-3'-O-(t-Butyldiphenylsilyl)-5'-Deoxy-2'-O-Methyladenosine, 76

Compound 75 will be treated and reacted with compound 50 as per the procedure of Example 39 to yield the title compound 76.

EXAMPLE 56

3'-De(oxophosphinico)-3'-[Methyl(iminooxymethylene)]-5'-Dimethoxytritylthymidylyl-(3'→5')-3'-[(S-
Cyanoethoxy)-N-(Diisopropyl)phosphiryl]-5'-
Deoxy-2'-O-Methyladenosine, 77

Compound 76 will be reacted as per the reaction sequence of Examples 40, 41 and 42 to yield the title compound 77.

EXAMPLE 57

6'-O-Amino-3'-O-(t-Butyldiphenylsilyl)-2'-Deoxy-5'-
Homoaristeromycin, 79

(−)-2'-Deoxy-5'-homoaristeromycin, compound 78, (the carbocyclic analogue of 5'-homo-2'-deoxyadenosine) is prepared as per the procedure of Jones, M. F. and Roberts, S. M., *J. Chem. Soc. Perkin Trans.*, 1:2927 (1988). Compound 78 will be treated as per the procedure of Examples 36, 37 and 38 to yield the 6'-O-amino-3'-blocked carbocyclic analogue of 5'-homo-2'-deoxyadenosine, compound 79.

EXAMPLE 58

3'-De(oxophosphinico)-3'-(Iminooxymethylene)-5'-Dimethoxytritylthymidylyl-(3'→5')-3'-O-(t-Butyldiphenylsilyl)-2',5'-Dideoxyaristeromycin, 80

Compound 79 will be treated and reacted with compound 50 as per the procedure of Example 39 to yield the title compound 80.

EXAMPLE 59

3'-De(oxophosphinico)-3'-[Methyl(iminooxymethylene)]-5'-Dimethoxytritylthymidylyl-(3'→5')-3'-[(β-Cyanoethoxy)-N-(Diisopropyl)phosphiryl]-2',5'-Dideoxyaristeromycin, 81

Compound 80 will be reacted as per the reaction sequence of Examples 40, 41 and 42 to yield the title compound 81.

EXAMPLE 60

6'-O-Amino-2'-O-Butyl-5'-Homoaristeromycin, 82

(−)-5'-Homoaristeromycin, compound 78, will be blocked with a TIPS group, alkylated and deblocked as per the procedure of Example 57 to yield compound 82.

EXAMPLE 61

6'-O-Amino-3'-O-(t-Butyldiphenylsilyl)-2'-O-Butyl-5'-Homoaristeromycin, 83

Compound 82 will be treated as per the procedures of Examples 36, 37 and 38 to yield the title compound 83.

EXAMPLE 62

3'-De(oxophosphinico)-3'-(Iminooxymethylene)-5'-Dimethoxytritylthymidylyl-(3'→5')-3'-O-(t-Butyldiphenylsilyl)-2'-O-Butyl-5'-Deoxyaristeromycin, 84

Compound 83 will be treated and reacted with compound 50 as per the procedure of Example 39 to yield the title compound 84.

EXAMPLE 63

3'-De(oxophosphinico)-3'-[Methyl(iminooxymethylene)]-5'-Dimethoxytritylthymidylyl-(3'→5')-3'-[(β-Cyanoethoxy)-N-(Diisopropyl)phosphiryl]-2'-O-Butyl-5'-Deoxyaristeromycin, 85

Compound 84 will be reacted as per the reaction sequence of Examples 40, 41 and 42 to yield the title compound 85.

EXAMPLE 64

(+)-1-[(1R,3S,4S)-3-Azido-5-Dimethoxytrityl-4-(Hydroxymethyl)-Cyclopentyl]-5-Methyl-2,4-(1H,3H)-Pyrimidindione, 87

(+)-1-[1R,3S,4S)-3-Azido-4-(hydroxymethyl)-cyclopentyl]-5-methyl-2,4-(1H,3H)-pyrimidindione, compound 86, prepared as per the procedure of Bodenteich, M. and Grieng, H., *Tetrahedron Letts.*, 28:5311 (1987), will be dimethoxytritylated utilizing dimethoxytrityl chloride in pyridine at room temperature to give the title compound 87.

EXAMPLE 65

(+)-1-[(1R,3S,4S)-3-Amino-4-(Dimethoxytrityloxymethyl)-Cyclopentyl]-5-Methyl-2,4-(1H,3H)-Pyrimidindione, 88

Compound 87 will be reduced with $Ph_3P$ in pyridine at room temperature as per the procedure of Hronowski, L. J. J. and Szarek, W. A., *J. Chem. Soc., Chem. Commun.*, 1547 (1990), to give the carbocyclic analogue of 3'-amino-5'-dimethoxytrityl thymidine, compound 88.

EXAMPLE 66

1-{(1R,3S,4S)-3-[Imino-2-(5'-Deoxythymidylyl-5'-yl)-1,2-Ethanediyl]-4-(Dimethoxtrityloxymethyl)-Cyclopentyl}-5-Methyl-2,4-(1H,3H)-Pyrimidindione, 89

Compound 88 will be reacted with compound 47 as per the procedure of Example 48 to yield the title compound 89.

EXAMPLE 67

Synthesis Of Oligonucleotides Using A DNA Synthesizer

Solid support oligonucleotide and "oligonucleotide like" syntheses are performed on an Applied Biosystems 380 B or 394 DNA synthesizer following standard phosphoramidite protocols and cycles using reagents supplied by the manufacture. The oligonucleotides are normally synthesized in either a 10 µmol scale or a 3×1 µmol scale in the "Trityl-On" mode. Standard deprotection conditions (30% $NH_4OH$, 55° C., 16 hr) are employed. HPLC is performed on a Waters 600E instrument equipped with a model 991 detector. For analytical chromatography, the following reverse phase HPLC conditions are employed: Hamilton PRP-1 column (15×2.5 cm); solvent A: 50 mm TEAA, pH 7.0; solvent B: 45 mm TEAA with 80% $CH_3CN$; flow rate: 1.5 ml/min; gradient: 5% B for the first 5 minutes, linear (1%) increase in B every minute thereafter. For preparative purposes, the following reverse phase HPLC conditions are employed: Waters Delta Pak Waters Delta-Pak $C_4$ 15 µm, 300A, 25×100 mm column equipped with a guard column of the same material; column flow rate: 5 ml/min; gradient: 5% B for the first 10 minutes, linear 1% increase for every minute thereafter. Following HPLC purification, oligonucleotides are detritylated and further purified by size exclusion using a Sephadex G-25 column.

EXAMPLE 68

HIGHER ORDER MIXED OLIGONUCLEOSIDES-OLIGONUCLEOSIDES AND MIXED OLIGONUCLEOSIDES-OLIGONUCLEOTIDES

A. Solution Phase Synthesis Of 3'-De(oxophosphinico)-3'-[Methyl(iminooxymethylene)]-Thymidylyl-(3'→5')-5'-Deoxythymidylyl-3'-Phosphorothioate-Thymidylyl-(3'→5')-3'-De(oxyphosphinico)-3'-[(Methylimino)-1,2-Ethanediyl]thymidylyl-(3'→5')-3'-O-(t-Butyldiphenylsilyl)-5'-Deoxythymidine, 90, A Mixed Oligonucleoside-Oligonucleotide-Oligonucleoside Polymer Incorporating A Nucleotide Linkage Flanked At Its 5' Terminus By A 3'-De(oxophosphinico)-3'-[Methyl(iminooxymethylene)] Linked Oligonucleoside Dimer and At Its 3' Terminus By A 3'-De(oxyphosphinico)-3'-[(Methylimino)-1,2-Ethanediyl] Linked Oligonucleoside Dimer A mixed oligonucleoside-oligonucleotide-oligonucleoside having a 3'-de(oxophosphinico)-3'-[methyl(iminooxymethylene)] linked oligonucleoside dimer and a 3'-de(oxyphosphinico)-3'-[(methylimino)-1,2-ethanediyl] linked oligonucleoside dimer coupled together via a phosphorothioate nucleotide linkage will be prepared by reacting compound 58, compound 70 and tetrazole in anhydrous acetonitrile under argon. The coupling reaction will be allowed to proceed to completion followed by treatment with Beaucage reagent and ammonium hydroxide removal of the dimethoxytrityl blocking group according to the procedure of Zon, G. and Stec, W. J., *Phosphorothioate oligonucleotides, Oligonucleotides and Analogs A Practical Approach*, F. Eckstein Ed., IRL Press, pg. 87 (1991). The 3' blocking group will then removed as per the procedure of Step 3 of Example 4 and the product purified by HPLC to yield the title compound 90, wherein utilizing the structure of Scheme XVIII, $T_3$ and $T_5$ are OH, D is S, E is OH, X is H, Q is O, r is 0 and q is 2; and for each q, i.e. $q_1$ and $q_2$, n and p are 1 in each instance; and for $q_1$, m is 1; and for $q_2$, m is 0; and Bxj and Bxi are thymine.

B. Solid Support Synthesis Of 3'-De(oxophosphinico)-3'-[Methyl(iminooxymethylene)]-Thymidylyl-(3'→5')-5'-Deoxythymidylyl-(3'→5')-P-Thymidylyl-3'-De(oxophosphinico)-3'-[Methyl(iminooxymethylene)]-(3'→5')-Thymidylyl-(3'→5')-P-Thymidylyl-3'-De(oxophosphinico)-3'-[Methyl(iminooxymethylene)]-(3'→5')-Thymidylyl-(3'→5')-P-2'-Deoxycytidine, 91, A Mixed Oligonucleotide-Oligonucleoside Polymer Incorporating 3'-De(oxophosphinico)-3'-[Methyl(iminooxymethylene)] Linked Oligonucleoside Dimers Flanked By Conventional Linked Nucleotides The dimeric oligonucleoside 58 will be utilized as building block units in a conventional oligonucleotide solid support synthesis as per the procedure of Example 67. For the purpose of illustration a polymer incorporating seven nucleosides is described. A first unit of the dimeric oligonucleoside 58 will be coupled to a first cytidine nucleoside tethered to a solid support via its 3' hydroxyl group and having a free 5' hydroxyl group. After attachment of the first unit of compound 58 to the support, the 5'-dimethoxytrityl group of that first compound 58 unit will be removed in the normal manner. A second compound 58 unit will then be coupled via its β-cyanoethyl-N-diisopropylphosphiryl group to the first compound 58 unit using normal phosphoramidate chemistry. This forms a conventional phosphodiester bond between the first and second compound 58 units and elongates the polymer by two nucleosides (or one oligonucleoside dimer unit). The dimethoxytrityl blocking group from the second compound 58 unit will be removed in the normal manner and the polymer elongated by a further dimeric unit of compound 58. As with addition of the first and second dimeric units, the third unit of compound 58 is coupled to the second via conventional phosphoramidite procedures. The addition of the third unit of compound 58 completes the desired length and base sequence. This polymer has a backbone of alternating normal phosphodiester linkages and the methyl(iminooxymethylene) linkages of compound 58. The 5' terminal dimethoxytrityl group of the third compound 58 unit will be removed in the normal manner followed by release of the polymer from the solid support, also in the normal manner. Purification of the polymer will be achieved by HPLC to yield compound 91 wherein, utilizing the structure of Scheme XVIII, $T_3$ and $T_5$ are OH, D is O, E is OH, X is H, Q is O, r is 1 and for the seven nucleoside polymer described, q is 3; and for each q, i.e. $q_1$, $q_2$ and $q_3$, n and p are 1 in each instances; and for $q_1$ and $q_2$, m is 1; and for $q_3$, m is 0; and Bxk is cytosine; and each BxJ and Bxi is thymine.

EVALUATION

PROCEDURE 1—Nuclease Resistance

A. Evaluation of the resistance of oligonucleotide-mimicking macromolecules to serum and cytoplasmic nucleases.

Oligonucleotide-mimicking macromolecules of the invention can be assessed for their resistance to serum nucleases by incubation of the oligonucleotide-mimicking macromolecules in media containing various concentrations of fetal calf serum or adult human serum. Labeled oligonucleotide-mimicking macromolecules are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide-mimicking macromolecules it is possible to determine the effect on nuclease degradation by the particular modification. For the cytoplasmic nucleases, an HL 60 cell line can be used. A post-mitochondrial supernatant is prepared by differential centrifugation and the labelled macromolecules are incubated in this supernatant for various times. Following the incubation, macromolecules are assessed for degradation as outlined above for serum nucleolytic degradation. Autoradiography results are quantitated for evaluation of the macromolecules of the invention. It is expected that the macromolecules will be completely resistant to serum and cytoplasmic nucleases.

B. Evaluation of the resistance of oligonucleotide-mimicking macromolecules to specific endo- and exo-nucleases.

Evaluation of the resistance of natural oligonucleotides and oligonucleotide-mimicking macromolecules of the invention to specific nucleases (ie, endonucleases, 3',5'-exo-, and 5',3'-exonucleases) can be done to determine the exact effect of the macromolecule linkage on degradation. The oligonucleotide-mimicking macromolecules are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the macromolecules linkage are determined for specific nucleases and compared with the results obtained from the serum and cytoplasmic systems. As with the serum and cytoplasmic nucleases, it is expected that the oligonucleotide-mimicking macromolecules of the invention will be completely resistant to endo- and exo-nucleases.

PROCEDURE 2—5-Lipoxygenase Analysis and Assays

A. Therapeutics

For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide-mimicking macromolecules of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics

The oligonucleotide-mimicking macromolecules of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotide-mimicking macromolecules which interfere with 5-lipoxygenase synthesis in these cells.

A second test system for oligonucleotide-mimicking macromolecules makes use of the fact that 5-lipoxygenase is a "suicide" enzyme in that it inactivates itself upon reacting with substrate. Treatment of differentiated HL-60 or other cells expressing 5 lipoxygenase, with 10 µM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotide-mimicking macromolecules can exert on intact cells and which can be easily be quantitated is specific inhibition of 5-lipoxygenase protein synthesis. To perform this technique, cells can be labelled with $^{35}$S-methionine (50 µCi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 µM, 10 µM, and 30 µM of the macromolecules of the invention for 48 hours would reduce immunoprecipitated 5-lipoxygenase by 5% 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 µM $^{14}$C-arachidonic acid, 2 mM ATP, 50 µM free calcium, 100 µg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 µM, 10 µM, and 30 µM would be as follows. Control cells oxidize 200 pmol arachidonic acid/5 min/10$^6$ cells. Cells treated with 1 µM, 10 µM, and 30 µM of an effective oligonucleotide-mimicking macromolecule would oxidize 195 pmol, 140 pmol, and 60 pmol of arachidonic acid/5 min/10$^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris•HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 μL in the microtiter wells for 90 min. The antibodies are prepared by immunizing rabbits with purified human recombinant 5-lipoxygenase. The wells are washed with TBS containing 0.05% tween 20 (TBST), then incubated with 100 μL of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide-mimicking macromolecule at 1 μM, 10 μM, and 30 μM would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells ($2\times10^5$ cells/mL) will be treated with increasing concentrations of the macromolecule for 48–72 hours in the presence of 1.3% DMSO. The cells are washed and resuspended at a concentration of $2\times10^6$ cell/mL in Dulbecco's phosphate buffered saline containing 1% delipidated bovine serum albumin. Cells are stimulated with 10 μM calcium ionophore A23187 for 15 min and the quantity of LTB4 produced from $5\times10^5$ cell determined by radioimmunoassay as described by the manufacturer.

Using this assay the following results would likely be obtained with an oligonucleotide-mimicking macromolecule directed to the 5-LO mRNA. Cells will be treated for 72 hours with either 1 μM, 10 μM or 30 μM of the macromolecule in the presence of 1.3% DMSO. The quantity of $LTB_4$ produced from $5\times10^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotide-mimicking macromolecules will be applied topically to both ears 12 to 24 hours prior to administration of arachidonic acid to allow optimal activity of the compounds. Both ears are pretreated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

We claim:

1. A nucleoside of the structure:

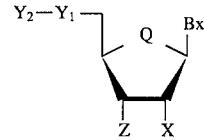

wherein $Y_1$ is $CH_2$;

$Y_2$ is aminooxy, alkylamino having 1 carbon atom, or alkenyl having 2 carbon atoms;

Z is H, OH, O—R'", amino, methyleneamino or phthalimido;

R'" is a hydroxyl blocking group;

X is H or OH;

Q is O; and

Bx is a heterocyclic base moiety.

2. The nucleoside of claim 1 wherein $Y_2$ is aminooxy.

3. The nucleoside of claim 1 wherein $Y_2$ is alkylamino having 1 carbon atom.

4. The nucleoside of claim 1 wherein $Y_2$ is alkenyl having 2 carbon atoms.

5. The nucleoside of claim 1 wherein Z is OH.

6. The nucleoside of claim 1 wherein Z is amino.

7. The nucleoside of claim 1 wherein Z is methyleneamino.

8. The nucleoside of claim 1 wherein Z is phthalimido.

* * * * *